United States Patent [19]

Tanaka et al.

[11] Patent Number: 4,876,261
[45] Date of Patent: Oct. 24, 1989

[54] SUBSTITUTED TETRAHYDROISOQUINOLINE COMPOUNDS AND COMPOSITION CONTAINING THEM

[75] Inventors: Akihiro Tanaka, Tokyo; Takashi Fujikura, Saitama; Ryuji Tsuzuki, Tokyo; Masaki Yokota, Saitama; Takeyuki Yatsu, Tokyo, all of Japan

[73] Assignee: Yamanouchi Pharmaceutical Co., Ltd., Tokyo, Japan

[21] Appl. No.: 173,376

[22] Filed: Mar. 25, 1988

[30] Foreign Application Priority Data

Mar. 27, 1987 [JP] Japan .................. 62-75437
May 25, 1987 [JP] Japan .................. 62-129368
Aug. 10, 1987 [JP] Japan .................. 62-200562
Aug. 10, 1987 [JP] Japan .................. 62-200563
Sep. 9, 1987 [JP] Japan .................. 62-226184
Sep. 10, 1987 [JP] Japan .................. 62-227398
Sep. 29, 1987 [JP] Japan .................. 62-247590
Oct. 7, 1987 [JP] Japan .................. 62-254012

[51] Int. Cl.$^4$ .................. A61K 31/47; C07D 217/16
[52] U.S. Cl. .................. 514/307; 546/114; 546/143; 546/144; 548/193; 548/195; 549/75; 558/410; 564/179; 564/365
[58] Field of Search .................. 546/143, 144; 514/307

[56] References Cited

U.S. PATENT DOCUMENTS

4,340,600  7/1982  Brenner et al. .................. 546/143

FOREIGN PATENT DOCUMENTS

1164192  9/1969  United Kingdom .................. 546/143

OTHER PUBLICATIONS

Jacob, et al., "J. Med. Chem.", vol. 24, No. 8, 1981, pp. 1013–1015.
Riggs, et al., "J. Med. Chem.", vol. 30, No. 8, 1987, pp. 1454–1458.

*Primary Examiner*—Richard L. Raymond
*Assistant Examiner*—James H. Turnipseed

[57] ABSTRACT

A compound of the formula (I) or its salt and a process for producing the compounds; The compounds have the effect to dilate neophrovascular tracts;

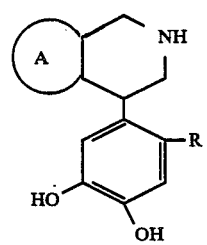

(I)

wherein

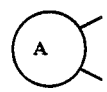

represents the formula

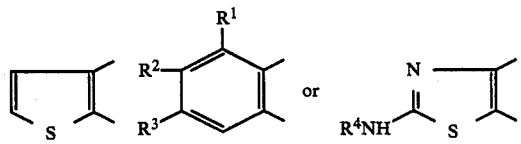

(wherein $R^4$ is a hydrogen atom or lower alkylsulfonyl);
$R^1$ is hydrogen, lower alkyl, hydroxyl, halogen, amino, or lower acylamino;
$R^2$ is hydrogen, lower alkyl, hydroxyl, amino, or lower alkylsulfonylamino;
$R^3$ is hydrogen, lower, alkyl or hydroxyl;
$R$ is hydrogen or halogen;

with the proviso that when $R^1$ is hydroxyl, there is no case that all of $R^2$, $R^3$ and $R$ are hydrogens, and further with the proviso that when $R$ is hydrogen, A excludes

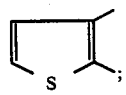

or a salt thereof.

8 Claims, No Drawings

SUBSTITUTED TETRAHYDROISOQUINOLINE COMPOUNDS AND COMPOSITION CONTAINING THEM

FIELD OF THE INVENTION

The present invention relates to a compound of the formula (I) or its salt and a process for producing the compounds; The compounds have the effect to dilate neophrovascular tracts;

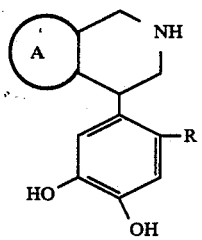
(I)

Wherein

represents the formula

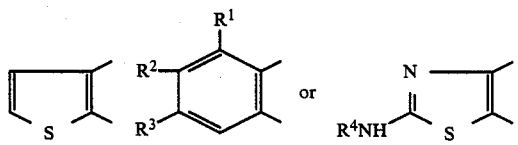

(wherein $R^4$ is a hydrogen atom or lower alkylsulfonyl);
$R^1$ is hydrogen, lower alkyl, hydroxyl, halogen, amino, or lower acylamino;
$R^2$ is hydrogen, lower alkyl, hydroxyl, amino, or lower alkylsulfonylamino;
$R^3$ is hydrogen, lower alkyl or hydroxyl;
R is hydrogen or halogen;
with the proviso that when $R^1$ is hydroxyl, there is no case that all of $R^2$, $R^3$ and R are hydrogens, and further with the proviso that when R is hydrogen, A excludes

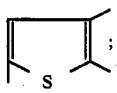

or a salt thereof.
(The above definitions in the formula (I) and groups are interpreted to be the same hereinafter). The compounds act directly upon dopamine receptor present in renal vascular tracts, and are used as nephrovascular dilators.

This invention relates to amino-substituted tetrahydroisoquinoline derivatives represented by the following general formula (I),

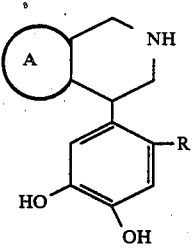
(I)

or salts thereof, which are compounds useful as medicines; to a process for preparing the same; and to medicines containing the same as active ingredient.

DESCRIPTION OF THE PRIOR ART

The kidney is an important organ which participates in maintaining homeostasis of the circulatory system. If blood circulation insufficiency occurs in this organ for some causes, renal functions will lower to break up homeostasis of the circulatory system, thus inducing, maintaining or aggravating diseases of circulatory organs, such as hypertension and cardiac insufficiency.

Vasodilators and diuretics have been used for the treatment of these diseases, but no vasodilator is so far known which has a positive effect to dilate renal vascular tracts. It is also known that conventional diuretics tend to upset the balance among electrolytes. Dopamine shows diuretic and nephrovascular dilating effects, but also has unfavorable effects (vasoconstricting and heart-rate increasing effects). In addition, it cannot be orally administered and its effect is not well maintained. Thus, there is no drug presently available which is suited for clinical use.

SUMMARY OF THE INVENTION

Under the circumstances, we have tried to develop new compounds which act directly upon dopamine receptor present in renal vascular tracts, and which can be orally administered and maintain the effect over long periods. This invention was accomplished on the basis of the result of such studies.

Thus, this invention relates to compounds represented by the general formula (I) and salts thereof, to a process for preparing the same, and to nephrovascular dilators containing the same as active ingredient.

The compounds of this invention have an asymmetric carbon atom at 4-position of the tetrahydroisoquinoline ring, and all the optical isomers based on this asymmetric carbon and mixtures thereof are included in this invention.

Compounds (I) are capable of forming salts, of which pharmacologically acceptable ones are also included in this invention. These are inorganic salts, such as hydrochlorides, hydrobromides, sulfates, phosphates and nitrates; and organic salts, such as maleates, fumarates, benzoates, ascorbates, methanesulfonates and tartrates.

DETAILED DESCRIPTION OF THE INVENTION

In the definition of the formula (I) compounds, "lower alkyl" means $C_1$ to $C_5$ straight or branched chain alkyl, and the examples of "lower alkyl" are methyl, ethyl, propyl, iso-propyl, butyl, iso-butyl, sec-butyl, pentyl, etc. "Lower acyl" means $C_1$ to $C_6$ straight or branched chain acyl, and the examples of "lower acyl" are formyl, acetyl, propionyl, butyryl, iso-butyryl, valeryl, iso-valeryl, pivaloyl, hexanoyl, etc. The examples of "halogen" are fluorine, chlorine, bromine or iodine. The compounds of this invention have an asymmetric carbon atom at 4-position of the tetrahydroisoquinoline ring, and, as the case may be, in lower alkyl and/or lower acyl, and all the optical isomers based on this asymmetric carbon and mixtures thereof are included in this invention.

Compounds (I) of this invention may be prepared by the methods described below.

METHOD 1

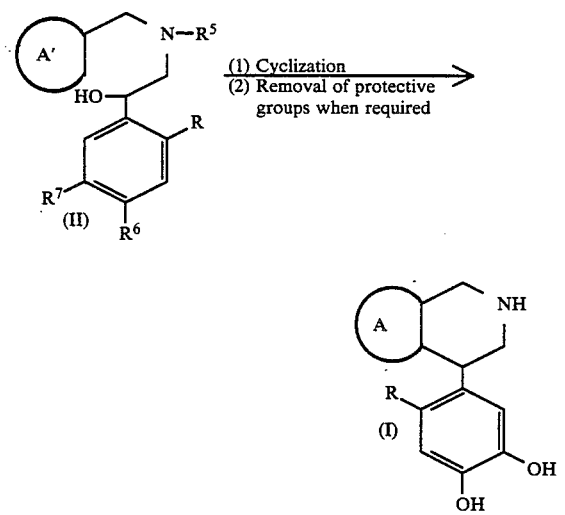

(wherein $R^6$ and $R^7$ are hydroxyl groups which may optionally be protected; and $R^5$ is hydrogen atom or a protective group for the nitrogen atom; A' is 2- (or 3-) thienyl, or other monovelent Ⓐ group.

This method comprises cyclization of a compound represented by the general formula (II), followed by removal of the protective groups when required. As examples of the protective groups for hydroxylis in the starting material (II), may be mentioned linear or branched lower alkyls such as methyl, ethyl, isopropyl and tert-butyl, and aralkyls such as benzyl and phenethyl. As the protective group for the nitrogen atom, may be used linear or branched lower alkyls such as methyl, ethyl, isopropyl and tert-butyl, aralkyls such as benzyl and phenethyl, and substituted or unsubstituted acyl groups such as acetyl and trifluoroacetyl. The above other monovelent Ⓐ means

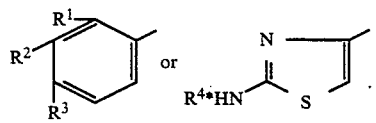

($R^{4*}$ may mean an amino-protective group in addition to the $R^4$ groups as defined before).

Compounds (I) can be prepared by subjecting a compound represented by the general formula (II) to intramolecular cyclization by the action of a cyclizing agent capable of forming carbonium ion from the alcoholic hydroxyl in compound (II), such as hydrochloric acid, sulfuric acid, sulfuric acid in trifluoroacetic acid, polyphosphoric acid, esters of polyphosphoric acid, methanesulfonic acid in dichloromethane, hydrogen bromide, and Lewis acids (e.g., boron trifluoride, aluminum chloride and stannic chloride).

There is no specific limitation upon the reaction temperature; the reaction is carried out under ice cooling or under reflux condition, with the reaction time being properly set in each case depending on other factors.

When the reaction product thus obtained contains protective groups, these are removed by catalytic reduction (e.g., catalytic hydrogenation) or by treatment with boron tribromide, hydrobromic acid, aluminum chloride, trimethylsilyl iodide or hydroiodic acid. The protective group on the nitrogen atom may be removed simultaneously with the protective groups on hydroxyl groups, or in a separate step (for example, by treatment with cyanogen bromide, hydrochloric acid or ammonia water, hydrogenation in the presence of a catalyst, or other suitable methods).

METHOD 2

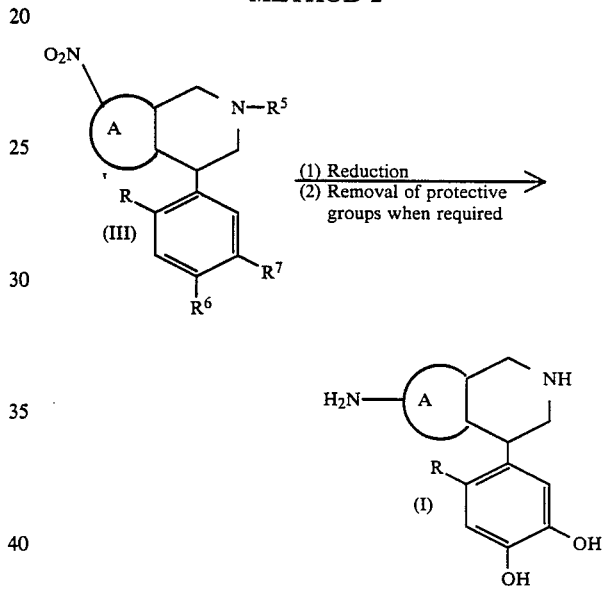

Compounds (I) of this invention can be prepared by reduction of a nitro compound represented by the general formula (III), followed by removal of the protective groups when required.

This reduction may be effected by the use of a sulfur compound, such as sodium sulfate, sodium hydrosulfide, sodium dithionite and ammonium sulfide; by catalytic reduction in the presence of platinum, platinum black, palladium-carbon (Pt-C) or Raney nickel, or by reduction using a metal hydride such as lithium aluminum hydride. Any solvents inert to the reaction may be used, including alcohols such as methanol, ethanol and isopropanol, tetrahydrofuran, diethyl ether, dioxane, benzene and toluene. The reaction is carried out at a temperature properly set depending on the type of reducing agent used (under ice cooling or at elevated temperatures). The protective groups of the nitrogen atom and hydroxyl groups can be simultaneously removed in this reducing step if the reaction is conducted under proper conditions.

The compounds (I) of this invention thus formed are isolated and purified in the form of free amine or a salt thereof by commonly employed techniques, for example, extraction, crystallization, recrystallization and various types of chromatography.

PREPARATIVE METHODS

Compounds (I) of this invention may be prepared by the methods described below.

METHOD 1'

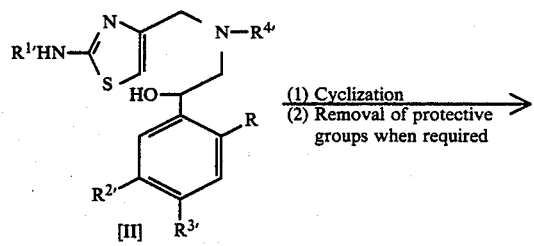

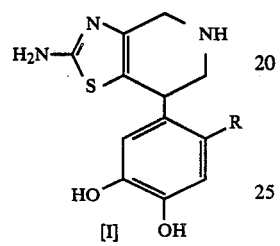

(wherein R is hydrogen atom or a halogen atom; $R^{1'}$ and $R^{4'}$ are each hydrogen atom or a protective group for the nitrogen atoms; and $R^{2'}$ and $R^{3'}$ are each hydroxyl group which may optionally be protected).

This method comprises cyclization of a compound represented by the general formula (II), followed by removal of the protective groups when required. As examples of the protective groups for hydroxyls in the starting material (II), may be mentioned linear or branched lower alkyls of 1 to 5 carbon atoms such as methyl, ethyl, isopropyl and tertbutyl, and aralkyls such as benzyl and phenetyl. As the protective groups for the nitrogen atoms, may be used tri(lower)alkylsilyl groups such as trimethylsilyl; acyl groups, such as formyl, acetyl, propionyl, trifluoroacetyl, tert-butoxycarbonyl, methoxyacetyl, methoxypropionyl and benzyloxycarbonyl; and aralkyls such as benzyl and benzhydryl.

Compounds (I) of this invention can be prepared by subjecting a compound represented by the general formula (II) to intramolecular cyclization by the action of a cyclizing agent capable of forming carbonium ion from the alcoholic hydroxyl in compound (II), such as hydrochloric acid, sulfuric acid, sulfuric acid in trifluoroacetic acid, polyphosphoric acid, esters of polyphosphoric acid, methanesulfonic acid in dichloromethane, hydrobromic acid, hydrogen fluoride, and Lewis acids (e.g., boron trifluoride, aluminum chloride and stannic chloride).

There is no specific limitation upon the reaction temperature; the reaction is carried out under ice cooling or under reflux condition, with the reaction time being properly set in each case depending on other factors.

When the reaction product thus obtained contains protective groups, these are removed by catalytic reduction (e.g., catalytic hydrogenation) or by treatment with boron tribromide, hydrobromic acid, aluminum chloride, trimethylsilyl iodide or hydroiodic acid. The protective groups on the nitrogen atoms may be removed simultaneously with the protective groups on hydroxyl groups, or in a separate step (for example, by treatment with cyanogen bromide, hydrochloric acid or ammonia water, hydrogenation in the presence of a catalyst, or other suitable methods).

METHOD 3

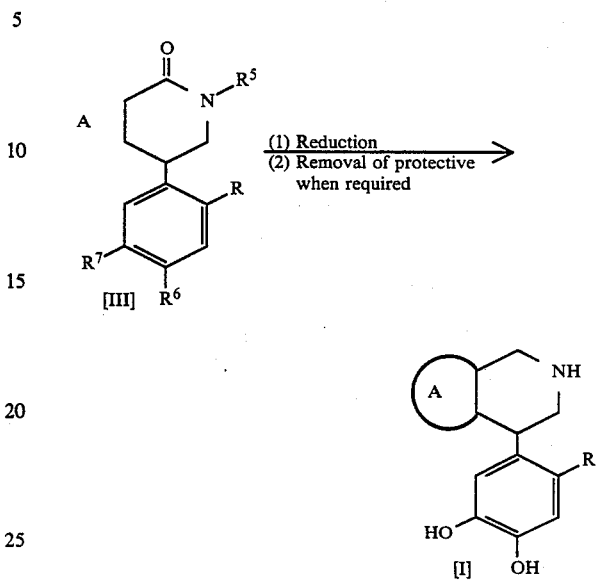

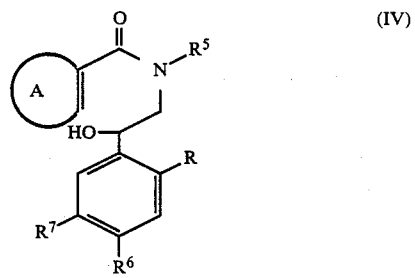

Compounds (I) of this invention can be prepared by reduction of a carbonyl compound represented by the general formula (III), followed by removal of the protective groups when required. The carbonyl compounds (III) used in this reaction may be obtained by subjecting an alcohol represented by the following general formula (IV)

$$\text{(IV)}$$

to intramolecular cyclization by the action of a cyclizing agent, such as hydrochloric acid, sulfuric acid, sulfuric acid in trifluoroacetic acid, polyphosphoric acid, esters of polyphosphoric acid, methanesulfonic acid in dichloromethane, hydrobromic acid, hydrogen fluoride, and Lewis acids (e.g., boron trifluoride, aluminum chloride and stannic chloride).

A carbonyl compound (III) thus obtained is treated with a reducing agent, such as borane, diborane, lithium aluminum hydride, sodium borohydride plus propionic acid, aluminum hydride diisobutyl and aluminum hydride bis(2-methoxyethoxy)sodium, and the protective groups are removed as required, giving a compound (I) of this invention. Any solvents inert to the reaction may be used, for example, tetrahydrofuran, diethyl ether, benzene and dioxane. The reaction is carried out at a temperature properly set depending on the type of reducing agent used (under ice cooling or at elevated temperatures). The protective groups can be removed by the methods described in Method 1.

The compounds (I) of this invention thus formed are isolated and purified in the form of free amine or a salt thereof by commonly employed techniques, for example, extraction, crystallization, recrystallization and various types of chromatography.

Compounds (I) of this invention and salts thereof are efficiently absorbed when administered orally because of the high liposolubility, and are effective for treating diseases of circulatory organs, such as renal insufficiency, cardiac insufficiency and hypertension.

Compounds (I) of this invention and salts thereof are efficiently absorbed when administered orally and are effective for treating diseases of circulatory organs, such as renal insufficiency, cardiac insufficiency and hypertension. In the treatment of hypertension, in particular, these compounds are expected to provide an etiologically effective medicine unlike conventional symptomatic drugs.

Compounds (I) of this invention and salts thereof have the effect to dilate nephrovascular tracts, and this action is exerted through dopamine receptor. Therefore, these compounds also have the effect to dilate vascular tracts of other organs, and directly act upon renal tubules, thus showing diuretic effect. In addition, these compounds are expected to be effective for the prevention of oliguria during and after operation and for the treatment of visceral hyperfunction, edemas, arterioscrelosis and blood coagulation.

The pharmacological effects were confirmed by the test described below.

TEST METHOD

Male and female mongrel dogs weighing 14 to 16 Kg were subjected to anesthesia with pentobarbital (30 mg/Kg i.v.), and artificial respiration was started by means of a cannula inserted into the trachea of each dog. During the whole course of test, pentobarbital was continuously administered (3 to 5 mg/Kg/hr) into the vein of right forelimb to maintain a constant anesthetic condition. A cannula for drug administration was inserted into the vein of right thigh. The systemic blood pressure was measured by means of a pressure transducer, with a cannula inserted into the artery of right thigh. The heart rate was measured using a cardiotachometer driven by pulse waveform.

Incision was made from the flank to the posterior wall of the peritoneum to expose the kidney, a probe was set to the renal artery, and the rate of renal blood flow was measured with an electromagnetic blood flowmeter. After setting the probe, an injection needle for drug administration connected to a polyethylene tube was inserted at the origin of the renal artery.

Each of the compounds tested was quickly injected in the form of a 0.2 ml solution, followed by continuous injection of physiological saline (0.5 ml/min) to ensure its rapid spreading in the renal artery.

All the test values are expressed as percentage change in the rate of blood flow, with the value immediately before administration taken as 100%.

Administration of the compounds of this invention to the renal artery of dogs put under anesthesia at doses of 0.3 to 100 μg showed increases in the rate of blood flow proportional to the amounts administered, with an increase of about 35% being observed at the highest dose. And, some compounds at doses of 0.3–30μg showed increases with an increase of about 40% being observed at the highest dose (30μg).

Preparations containing, as active ingredient, at least one of the compounds (I) and salts thereof of this invention may be manufactured in the form of tablets, powder, beadlets, granules, capsules, pills, injections, suppositories, ointment or poultices by using carriers, excipients and other commonly employed additives, and are orally (including sublingual application) or parenterally administered.

The suitable daily dose of the compounds of this invention should be determined with consideration given to the physical conditions, body weight, age, sex and other factors of particular patients, but is normally 50 to 1000 mg for adults (given all at a time or subdivided in several doses).

REFERENCE EXAMPLE A

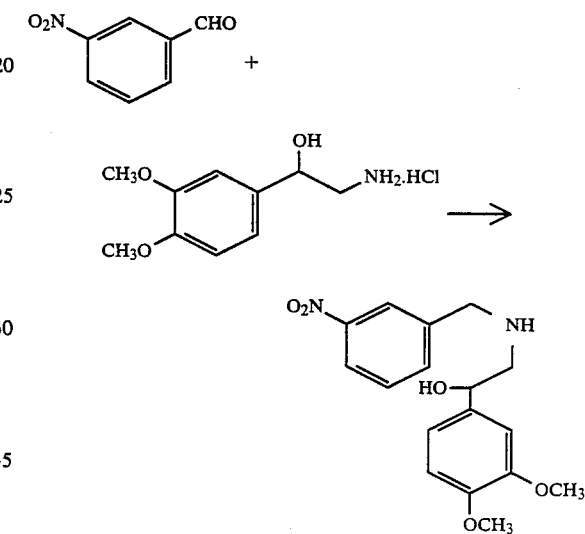

m-Nitrobenzaldehyde (1.8 g) was added to a suspension of α-(aminomethyl)-3,4-dimethoxybenzyl alcohol hydrochloride in 25 ml methanol, triethylamine (2.8 ml) was further added dropwise at room temperature with stirring, and the resulting solution was heated under reflux for 30 minutes. After cooling, sodium borohydride (1.45 g) was added in small portions with stirring under ice cooling, and the mixture was stirred at room temperature for one hour and concentrated. The residue was treated with chloroform and water, and the chloroform layer was collected, washed with water and dried over anhydrous sodium sulfate. The solvent was distilled off, and the residue was recrystallized from ether/n-hexane, affording 3.3 g of pure α-[(3-nitrobenzylamino)methyl]-3,4-dimethoxybenzyl alcohol, m.p. 105°–107° C.

REFERENCE EXAMPLE B

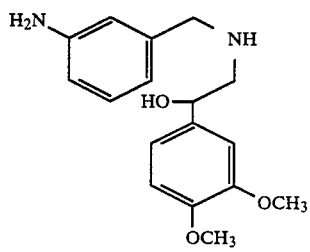

To a solution of 3.3 g α-[(3-nitrobenzylamino)methyl]-3,4-dimethoxybenzyl alcohol obtained in Reference Example 1 in 50 ml methanol, was added 0.6 g Raney nickel, and the mixture was subjected to hydrogenation at room temperature. After confirming complete absorption of hydrogen gas, the reaction mixture was filtered, the filtrate was concentrated, and the residue was recrystallized from ethyl acetate.

REFERENCE EXAMPLE 1

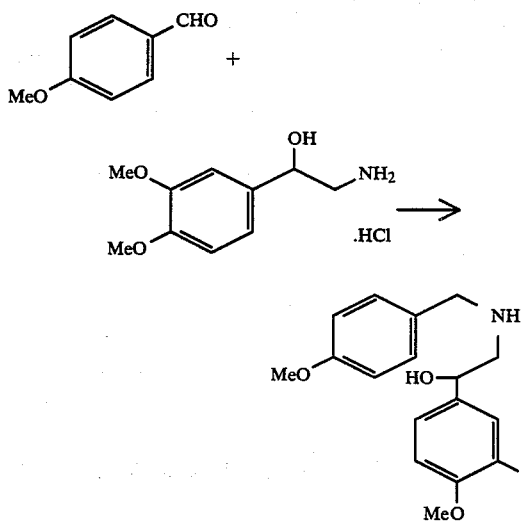

α-[[(4-methoxybenzyl)amino]methyl]-3,4-dimethoxybenzyl alcohol (m.p. 110°–112° C.)

REFERENCE EXAMPLE 2

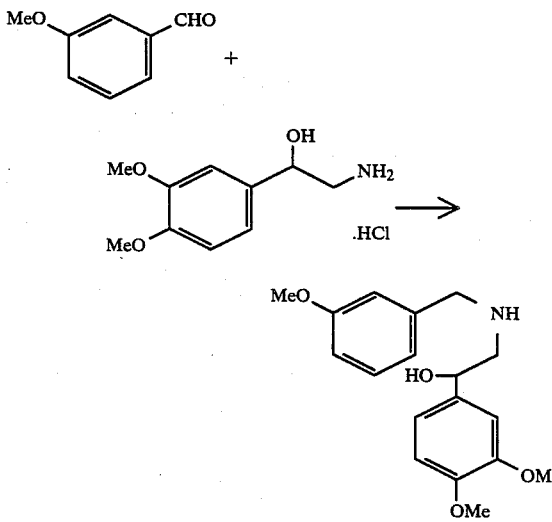

α-[[(3-methoxybenzyl)amino]methyl]-3,4-dimethoxybenzyl alcohol (m.p. 115°–116° C.)

REFERENCE EXAMPLE 3

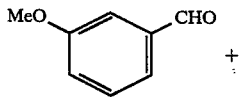

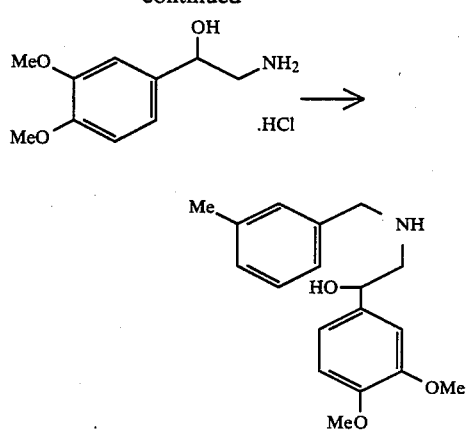

α-[[(3-methylbenzyl)amino]methyl]-3,4-dimethoxybenzyl alcohol.

REFERENCE EXAMPLE 4

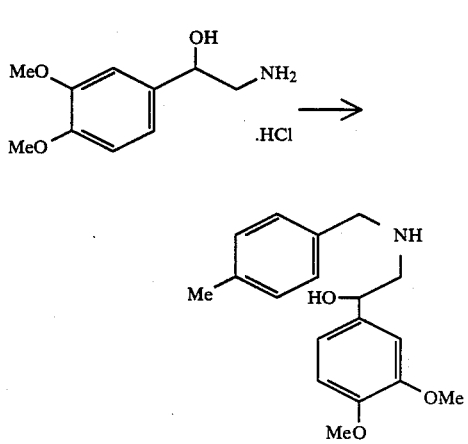

α-[[(4-methylbenzyl)amino]methyl]-3,4-dimethoxybenzyl alcohol.

REFERENCE EXAMPLE 5

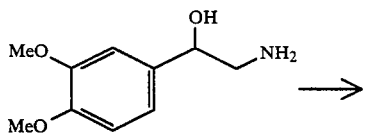

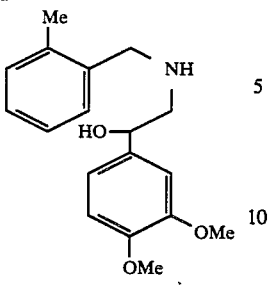

α-[[(2-methylbenzyl)amino]methyl]-3,4-dimethoxyben-zylalcohol (m.p. 103°–104° C.)

REFFERENCE EXAMPLE 6

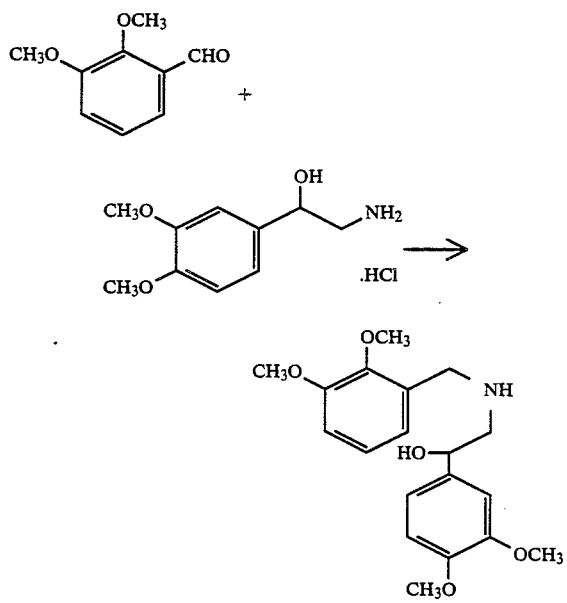

1.0 g of α-(aminomethyl)-3,4-dimethoxybenzyl alcohol hydrochloride was suspended in 5 ml of methanol, and after adding thereto 0.85 of 2,3-dimethoxybenzalde- hyde, 0.63 ml of triethylamine was added dropwise to the mixture while stirring at room temperature. The mixture was heated under reflux for 30 minutes, and 0.24 g of sodium boron hydride was added slowly to the mixture while stirring under ice cooling. After the foaming stopped, the mixture was concentrated. The residue was subjected to a separating procedure with chloroform and water, the chloroform layer was collected, washed with water, and dried over anhydrous sodium sulfate. The solvent was distilled off, and the residue was recrystallized from ethyl acetate-n-hexane, giving 1.07 g of α-[[(2,3-dimethoxybenzyl)amino]methyl]-3,4-dimethoxybenzyl alcohol, m.p. 96°–97° C.

REFERENCE EXAMPLE 7

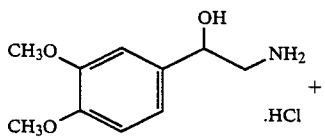

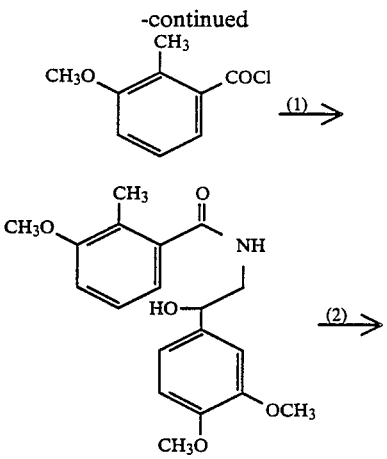

(1) To 1.56 g of 3-methoxy-2-methybenzoic acid, was added 2.03 g of thionyl chloride, and the mixture was heated under reflux for 30 minutes. The reaction solution was concentrated, and subjected to azeotropic distillation with toluene 2 times. The residue was dissolved in 8 ml of toluene, and the solution was added dropwise to a mixture of 2.0 g of α-(aminomethyl)-3,4-dimethoxybenzyl alcohol hydrochloride and 1.52 ml of pyridine and 20 ml of isopropyl alcohol under ice cooling while stirring. The temperature of the mixture was reverted to room temperature, and after 30 minutes, the reaction solution was concentrated. The residue was dissolved in ethyl acetate, washed with 1N aqueous HCl, saturated aqueous NaHCO$_3$ solution, and water, successively, and dried over anhydrous sodium sulfate. The solvent was distilled off, and the residue was recrystallized from ethyl acetate-n-hexane, giving 2.41 g of α-[N-(3-methoxy-4-methylbenzoyl)amidomethyl]-3,4-dimethoxybenzyl alcohol, m.p. 106°–109° C. (2) 1.02 g of α-[N-(3-methoxy-4-methylbenzoyl)amidomethyl]-3,4-dimethoxybenzyl alcohol was dissolved in 10 ml of tetrahydrofuran, and 1M boran-tetrahydrofuran solution (10.8 ml) was added dropwise to the mixture under an argon gas stream under ice cooling. The mixture was heated under reflux for 2.5 hours, and after ice cooling, 0.44 ml of methanol was added dropwise, and the mixture was heated under reflux for 30 minutes. The mixture was cooled with ice, and after adding thereto 0.9 ml of conc. hydrochloric acid, the mixture was heated under reflux for 30 minutes, and concentrated. The residue was dissolved in water, washed with ether twice, and basified, and extracted with chloroform twice. The chloroform layers were collected, washed with water, and dried over anhydrous sodium sulfate. The solvent was distilled off, and the residue was recrystallized from chloroform-n-hexane, giving 560 mg of α-[[(3-methoxy-2-methylbenzyl)amino]methyl]-3,4-dimethoxybenzyl alcohol, m.p. 135°–136° C.

REFERENCE EXAMPLE 8

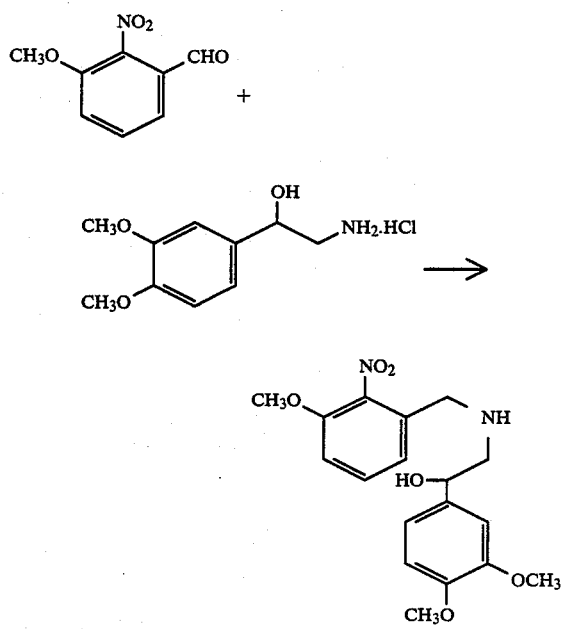

α-[[(3-methoxy-2-nitrobenzyl)amino]methyl]-3,4-dimethoxybenzyl alcohol (m.p. 92°–94° C.)

REFERENCE EXAMPLE 9

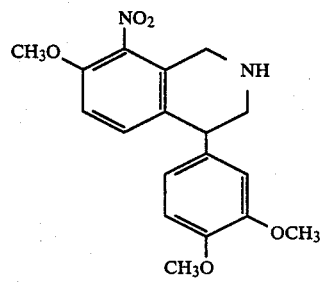

4(3,4-dimethoxyphenyl)-7-methoxy-8-nitro-1,2,3,4-tetrahydroisoquinoline.

REFERENCE EXAMPLE 10

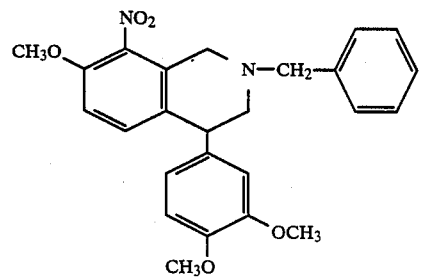

2-Benzyl-4-(3,4-dimethoxyphenyl)-7-methoxy-8-nitro-1,2,3,4-tetrahydroisoquinoline (m.p. 118°–119° C.)

REFERENCE EXAMPLE 11

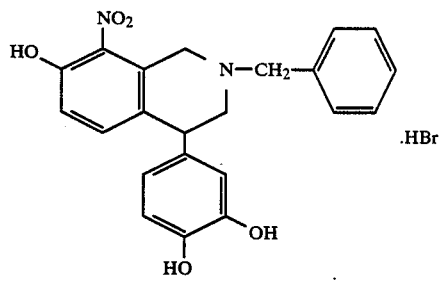

2-Benzyl-4-(3,4-dihydroxyphenyl)-7-hydroxy-8-nitro-1,2,3,4-tetrahydroisoquinoline hydrobromide (m.p. above 180° C. (decomposition))

REFERENCE EXAMPLE 12

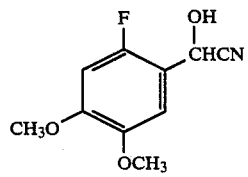

α-(cyano)-6-fluoro-3,4-dimethoxybenzyl alcohol.

REFERENCE EXAMPLE 13

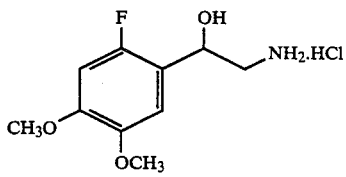

α-(aminomethyl)-6-fluoro-3,4-dimethoxybenzyl alcohol hydrochloride (m.p. 223°–226° C.)

REFERENCE EXAMPLE 14

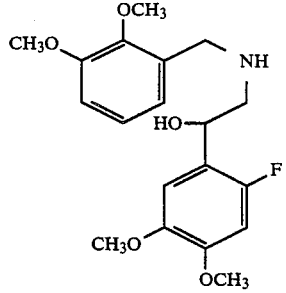

α-[[(2,3-dimethoxybenzylamino]methyl-6-fluoro-3,4-dimethoxybenzyl alcohol (m.p. 110°–112° C.)

REFERENCE EXAMPLE 15

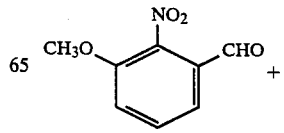

-continued

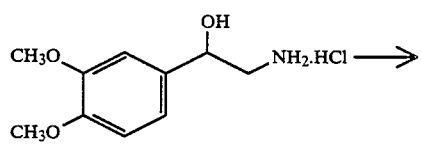

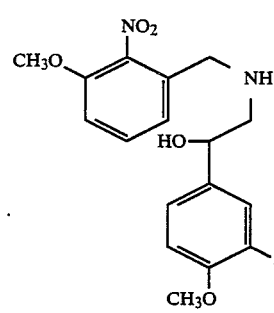

α-[[(3-methoxy-2-nitrobenzyl)amino]methyl]-3,4-dimethoxybenzyl alcohol (m.p. 92°–94° C.)

REFERENCE EXAMPLE 16

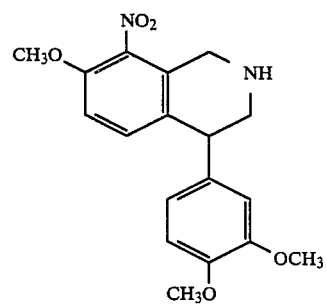

4-(3,4-dimethoxyphenyl)-7-methoxy-8-nitro-1,2,3,4-tetrahydroisoquinoline.

REFERENCE EXAMPLE 17

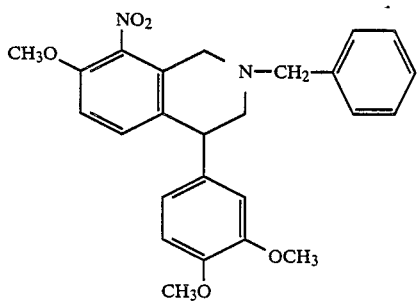

2-benzyl-4-(3,4-dimethoxyphenyl)-7-methoxy-8-nitro-1,2,3,4-tetrahydroisoquinoline (m.p. 118°–119° C.)

REFERENCE EXAMPLE 18

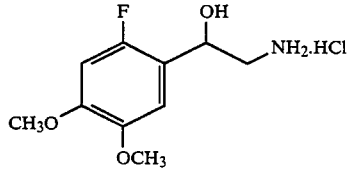

8-amino-2-benzyl-7-methoxy-4-(3,4-dimethoxyphenyl)-1,2,3,4-tetrahydroisoquinoline (m.p. 142°–143° C.)

REFERENCE EXAMPLE 19

α-(cyano)-6-fluoro-3,4-dimethoxybenzyl alcohol (m.p. 112°–114° C.)

REFERENCE EXAMPLE 20

α-(aminomethyl)-6-fluoro-3,4-dimethoxybenzyl alcohol hydrochloride (m.p. 223°–226° C.)

REFERENCE EXAMPLE 21

α-[(benzylamino)methyl]-6-fluoro-3,4-dimethoxybenzyl alcohol (m.p. 80°–82.5° C.)

REFERENCE EXAMPLE 22

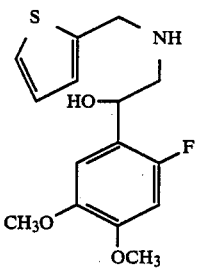

α-[[(2-thenyl)amino]methyl]-6-fluoro-3,4-dimethoxybenzyl alcohol (m.p. 79°–83° C.)

REFERENCE EXAMPLE 23

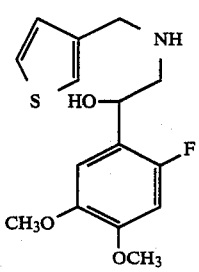

α-[[(3-thenyl)-amino]methyl]-6-fluoro-3,4-dimethoxybenzyl alcohol (a syrupy matter)

REFERENCE EXAMPLE 24

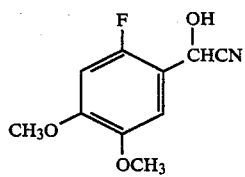

α-(cyano)-6-fluoro-3,4-dimethoxybenzyl alcohol (m.p. 112°–114° C.)

REFERENCE EXAMPLE 25

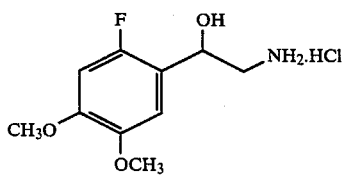

α-(aminomethyl)-6-fluoro-3,4-dimethoxybenzyl alcohol (m.p. 223°–226° C.)

REFERENCE EXAMPLE 26

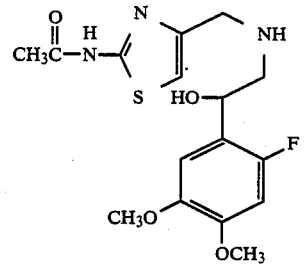

α-[[[(2-acetamido-4-thiazolyl)methyl]amino]methyl]-6-fluoro-3,4-dimethoxybenzyl alcohol (m.p. 173°–175° C.)

REFERENCE EXAMPLE 27

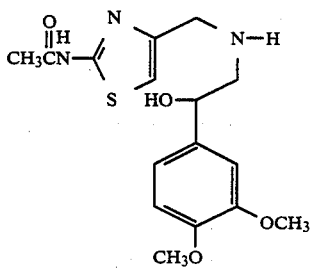

α-[[[2-acetamido-4-thiazolyl)methyl]amino]methyl]-3,4-dimethoxybenzyl alcohol (m.p. 204°–206° C.)

REFERENCE EXAMPLE 28

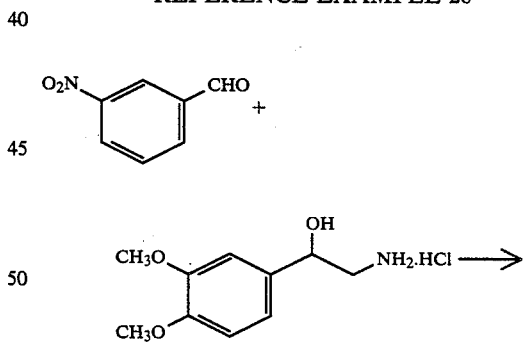

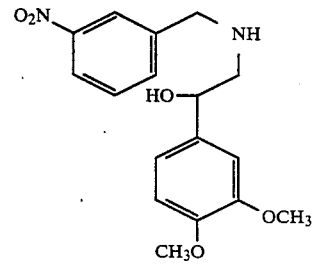

α-[(3-nitrobenzylamino)methyl]-3,4-dimethoxybenzyl alcohol (m.p. 105°–107° C.)

REFERENCE EXAMPLE 29

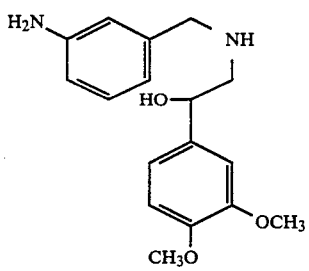

α-[(3-aminobenzylamino)methyl]-3,4-dimethoxybenzyl alcohol (m.p. 84°–86° C.)
(The above Reference Examples compounds were prepared by conventinal manners.)

EXAMPLE 1

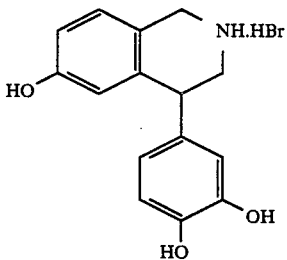

(1) α-[[(4-methoxybenzyl)amino]methyl]-3,4-dimethoxybenzyl alcohol (950 mg) was dissolved in 7.2 ml of trifluoroacetic acid, and after adding thereto 0.22 ml of conc. sulfuric acid under cie cooling, the reaction was allowed to react for 45 minutes. The reaction solution was concentrated, and subjected to azeotropic distillation with toluene 2 times. After adding chloroform, the mixture was basified by addition of 28% aqueous amminoa under ice cooling. By a separating procedure, the chloroform layer was collected, washed with water, and dried over anhydrous sodium sulfate. The solvent was distilled off, and the residue obtained was subjected to silica gel column chromatography (chlroform-methanol28% aqueous ammonia=15:1:0.1), giving 790 mg of 6-methoxy-4-(3,4-dimethoxyphenyl)-1,2,3,4-tetrahydroisoquinoline as oily matter.

(2) To 790 mg of 6-methoxy-4-(3,4-dimethoxyphenyl)-1,2,3,4-tetrahydroisoquinoline, was added 16 ml of 48% hydrobromic acid, and the mixture was heated under reflux for 3 hours under an argon stream. The reaction solution was cooled, and precipitates which separated out were collected by filtration, giving 630 mg of 6-hydroxy-4-(3,4-dihydroxyphenyl)-1,2,3,4-tetrahydroisoquinoline hydrobromide.

Elemental analysis (as $C_{15}H_{16}NO_3Br$)

| | Elemental analysis (as $C_{15}H_{16}NO_3Br$) | | | |
|---|---|---|---|---|
| | C (%) | H (%) | N (%) | Br (%) |
| Calcd. | 53.27 | 4.77 | 4.14 | 23.63 |
| Found | 53.16 | 4.70 | 4.16 | 23.35 |

Melting point : above 250° C.
Mass spectrum (FAB) 258 (M++1)
NMR spectrum (d6-DMSO, internal standard TMS)
δ(ppm) 3.24 (1H,d), 3.49 (1H, dd), 6.23 (1H, d), 6.59 (1H, s) 6.74 (1H, s), 6.76 (1H, d) 7.40 (1H, d)

EXAMPLE 2

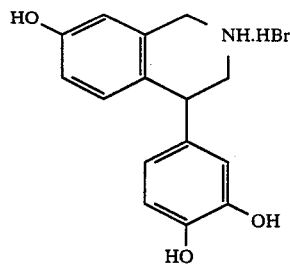

(1) 17.5 ml of α-[[(3-methoxybenzyl)amino]methyl]-3,4-dimethoxybenzyl alcohol was dissolved in 17.5 ml of trifluoroacetic acid, and after adding thereto 5.4 ml of conc. sulfuric acid under ice cooling, the reaction was allowed to react for 60 minutes. The reaction solution was concentrated, and was subjected to azeotropic distillation with toluene 2 times. After adding chloroform, the mixture was basified by addition of 28% aqueous ammonia under ice cooling. By a separating procedure, the chloroform layer was collected, washed with water once, and dried over anhydrous sodium sulfate. The solvent was distilled off, and the residue was subjected to silica gel colum chromatography (chloroform-methanol-28% aqueous ammonia=15:1:0.1), a material of Rf being 0.47 and 0.35 [Kiesel gel 60F$_{254}$ plate; chloroform-methanol-28% aqueous ammonia (15:1:0.1)]was obtained. The material of Rf being 0.47 is 5-methoxy-4-(3,4-dimethoxyphenyl)-1,2,3,4-tetrahydroisoquinoline (m.p. 118°–119° C., recrystallized from chloroform-n-hexane) (680 mg), and the material of Rf being 0.35 is 7-methoxy-4-(3,4-dimethoxyphenyl)-1,2,3,4,-tetrahydroisoquinoline (m.p. 119°–120° C., ethyl acetate-n-hexane recrystallization) (670 mg).

(2) 640 mg of 7-methoxy-4-(3,4-dimethoxyphenyl)-1,2,3,4-tetrahydroisoquinoline was dissolved in 13 ml of 48% aqueous hydrogen bromide, and the mixture was heated under reflux under an argon gas stream for 3 hours. The reaction solution was cooled, and crystals which separated out were collected, affording 580 mg of 7-hydroxy4-(3,4-dihydroxyphenyl)-1,2,3,4,-tetrahydroisoquinoline hydrobromide.

Elemental analysis (as $C_{15}H_{16}NO_3Br$. 1/5 $H_2O$)

| | C(%) | H(%) | N(%) | Br(%) |
|---|---|---|---|---|
| Calcd. | 52.71 | 4.84 | 4.10 | 23.38 |
| Found | 52.66 | 4.79 | 4.07 | 23.63 |

Melting point: above 220° C. (decomposition)
Mass spectrum (FAB) 258 (M++1)
NMR spectrum (d6-DMSO, internal standard TMS)
δ(ppm): 3.22 (1H, d), 3.48 (1H, dd), 4.60 (1H, dd), 6,58 (1H, s), 6.64 (1H, s), 6.67 (1H, d)

EXAMPLE 3

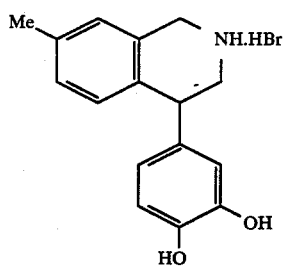

(1) 1.8 g of α-[[(3-methylbenzyl)amino]methyl]-3,4-dimethoxybenzyl alcohol was dissolved in 13.5 ml of trifluoroacetic acid, and after adding thereto 0.41 ml of conc. sulfuric acid under ice cooling, the mixture was allowed to react for 40 minutes. The reaction solution was concentrated, and subjected to azeotropic distillation with chloroform 2 times, and after adding chloroform, the mixture was basified by addition of 28% aqueous ammonia. By a separating procedure, the chloroform layer was collected, washed with water once, and dried over anhydrous sodium sulfate. The solvent was distilled off, and the residue was subjected to silica gel column chromatography (chloroform-methanol-28% aqueous ammonia (15:1:0.1); a material of Rf being 0.46 [Kiesel gel 60F$_{254}$ plate, chloroform-methanol-28% aqueous ammonia (15:1:0.1)]was collected, recrystallized from chloroform-n-hexane, and recrystallized from the same solvent system several times, giving 870 mg of 4-(3,4-dimethoxyphenyl)-7-methyl-1,2,3,4-tetrahydroisoquinoline, m.p. 129°–131° C.

(2) 850 mg of 4-(3,4-dimethoxyphenyl)-7-methyl-1,2,3,4-tetrahydroisoquinoline was dissolved in 17 ml of 48% hydrobromic acid, and the mixture was heated under reflux under an argon gas stream for 3 hours. The reaction solution was cooled, and the crystals obtained were collected by filtration, giving 620 mg of 4-(3,4-dihydroxyphenyl)-7-methyl-1,2,3,4-tetrahydroisoquinoline hydrobromide.

Melting point; 192°–195° C.

Elemental analysis (as C$_{15}$H$_{16}$NO$_3$Br)

|        | C(%)  | H(%) | N(%) | Br(%) |
|--------|-------|------|------|-------|
| Calcd. | 57.16 | 5.40 | 4.17 | 23.76 |
| Found  | 57.21 | 5.29 | 4.03 | 23.83 |

Mass spectrum (FAB) 256 (M$^+$=1)

NMR spectrum (d$_6$-DMSO, internal standard TMS) δ(ppm): 2.27 (3H, s), 3.26 (1H, dd), 3.59 (1H, dd) 6.48 (1H, dd), 6.55 (1H, s), 6.72 (1H, dx2), 7.02 (1H, d), 7.08 (1H, s)

EXAMPLE 4

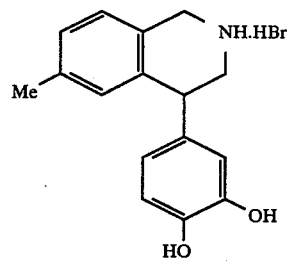

530 mg of α-[[(4-methylbenzyl)amino]methyl]-3,4-dimethoxybenzyl alcohol was dissolved in 4 ml of trifluoroacetic acid, and after adding thereto 0.12 ml of conc. sulfuric acid under ice cooling, the mixture was allowed to react for 30 minutes. The reaction solution was concentrated, and subjected to azeotropic distillation with toluene 2 times. After adding chloroform, the mixture was basified by addition of 28% aqueous ammonia. By a separating procedure, the chloroform layer was collected, was washed with water once, and dried over anhydrous sodium sulfate. The solvent was distilled off, and the residue was recrystallized from ethyl acetate-n-hexane, giving 490 mg of 4-(3,4-dimethoxyphenyl)-6-methyl-1,2,3,4-tetrahydroisoquinoline (melting point: 94°–96° C.). (2) To 450 mg of 4-(3,4-dimethoxyphenyl)-6-methyl-1,2,3,4-tetrahydroisoquinoline, was added 9 ml of 48% hydrobromic acid, and the mixture was heated under reflux under an argon gas stream for 3 hours. The reaction solution was cooled, and the crystals which separated out were collected by filtration, giving 390 mg of 4-(3,4-dihydroxyphenyl)-6-methyl-1,2,3,4-tetrahydroisoquinoline hydrobromide.

Melting point above 250° C. (decomposition)

Elemental analysis (as C$_{15}$H$_{16}$NO$_3$Br)

|        | C(%)  | H(%) | N(%) | Br(%) |
|--------|-------|------|------|-------|
| Calcd. | 57.16 | 5.40 | 4.17 | 23.76 |
| Found  | 56.95 | 5.44 | 4.02 | 24.06 |

Mass spectrum (EI) 255 (M$^+$)

NMR spectrum (d$_6$-DMSO, internal standard TMS) δ(ppm): 2.20 (3H, s), 3.28 (1H, dd), 3.64 (1H, dd), 6.50 (1H, dd), 6.56 (1H, dd), 6.56 (1H, s), 6.64 (1H, s), 6.75 (1H, d), 7.04 (1H, dd), 7.18 (1H, d)

EXAMPLE 5

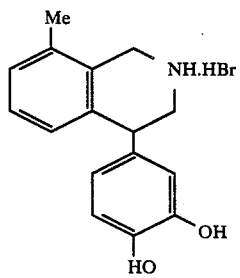

(1) 900 mg of α-[[(2-methoxybenzylamino]methyl]-3,4-dimethoxybenzyl alcohol was dissolved in 7 ml of trifluoroacetic acid, and after adding thereto 0.21 ml of conc. sulfuric acid under ice cooling, the mixture was allowed to react for 60 minutes. The reaction solution was concentrated, and subjected to zzeotropic distillation 3 times, and after adding chloroform, the mixture was basified by addition of 28% aqueous ammonia. By a separating procedure, the chloroform layer was collected, washed with water, and dried over anhydrous sodium sulfate. The solvent was distilled off, and the residue obtained was recrystallized from ethyl acetate-n-hexane, giving 440 mg of 4-(3,4-dimethoxyphenyl)-8-methyl-1,2,3,4-tetrahydroisoquinoline, m.p. 86°–88° C.

(2) To 420 mg of 4-(3,4-dimethoxyphenyl)-8-methyl-1,2,3,4-tetrahydroisoquinoline, was added 48% hydrobromic acid, and the mixture was heated under reflux for 3 hours. After about 10 minutes, the crystals becomes to be separated out. The reaction mixture was cooled, and the crystals were collected by filtration, giving 420 mg of 4-(3,4-dihydroxyphenyl)-8-methyl-1,2,3,4-tetrahdyroisoquinoline hydrobromide.

Melting point: above 250° C. (decomposition)
Elemental analysis (as $C_{15}H_{16}NO_3Br$)

|  | C(%) | H(%) | N(%) | Br(%) |
|---|---|---|---|---|
| Calcd. | 57.16 | 5.40 | 4.17 | 23.76 |
| Found | 57.04 | 5.43 | 4.17 | 23.73 |

Mass spectrum (FAB) 256 (M+ =L)
NMR spectrum (d$_6$-DMSO, internal standard TMS)
δ(ppm): 2.28 (3H, s), 3.60 (1H, dd), 6.50 (1H, dd), 6.80 (1H, s), 6.65 (1H, d), 6.76 (1H, d), 7.12 (1H, d)

EXAMPLE 6

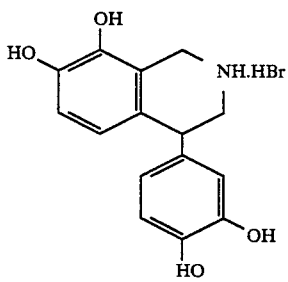

(1) 1.0 g of α-[2,3-dimethoxybenzyl)amino]methyl]-3,4-dimethoxybenzyl alcohol was dissolved in 7.5 ml of trifuluoroacetic acid, and after adding thereto 0,23 ml of conc. sulfuric acid under ice cooling, the mixture was allowed to react for 30 minutes. The reaction solution was concentrated, and subjected to azeotropic distillation with toluene 2 times. After adding to the mixture chloroform, the mixture was basified by addition of 28% aqueous ammonia under ice cooling. After separating procedure, the chloroform layer was collected, washed with water, and dried over anhydrous magnesium sulfate. The solvent was distilled off, and the residue thus obtained was recrystallized from chloroform-n-hexane, affording 750 mg of 7,8-dimethoxy-4-[3,4-dimethoxyphenyl)-1,2,3,4-tetrahydroisoquinoline, m.p. 109°–110° C.

(2) To 700 mg of 7,8-dimethoxy-4-(3,4-dimethoxyphenyl)-1,2,3,4-tetrahydroisoquinoline, was added 14 ml of 48% hydrobromic acid, and the mixture was heated under reflux for 3 hours under an argon gas stream. The reaction mixture was cooled, and the crystals which separated ount were collected by filtration, giving 540 mg of 7,8-dihydroxy-4-(3,4-dihydroxyphenyl)-1,2,3,4-tetrahydroisoquinoline hydrobromide.

Elemental analysis (as $C_{15}H_{16}NO_4Br$)

|  | C(%) | H(%) | N(%) | Br(%) |
|---|---|---|---|---|
| Calcd. | 50.87 | 4.55 | 3.95 | 22.56 |
| Found | 51.02 | 4.33 | 3.96 | 22.82 |

Melting point: above 230° C. (decomposition)
Mass spectrum (FAB) 274 (M+ +1)
NMR spectrum (d-DMSO; internal standard: TMS)
δ(ppm) 3.24. (1H, m), 3.52 (1H, m), 6.08 (1H, d), 6.48 (1H, dd), 6.58 (1H, s), 6.68 (1H, d), 6.76 (1H, d)

EXAMPLE 7

510 mg of α-[[(3-methoxy-2-methylbenzyl)amino]methyl]-3,4-dimethoxybenzyl alcohol was dissolved in 3.8 ml of trifluoroacetic acid, 0.12 ml of conc. sulfuric acid was added dropwise under ice cooling, and the mixture was allowed to react for 30 minutes. The reaction solution was concentrated, and subjected to azeotropic distillation with toluene 2 times. The residue was dissolved in chloroform, and basified by addition of 28% aqueous ammonia. The chloroform layter was collected, washed with water, and dried over anhydrous magnesium sulfate. The solvent was distilled off, and the residue was recrystallized from ethyl acetate-n-hexane, giving 430 mg of 7-methoxy-4-(3,4-dimethoxyphenyl)-8-methyl-1,2,3,4-tetrahydroisoquinoline, m.p. 128°–129° C. (2) To 410 mg of 7-methoxy-4-(3,4-dimethoxyphenyl)-8-methyl-1,2,3,4-tetrahydroixoquinoline, was added 8.2 ml of 48% hydrobromic acid, and the mixture was heated under reflux under an argon gas stream for 3 hours. The reaction mixture was cooled, and the crystals which separated out were collected by filtration, giving 410 mg of 7-hydroxy-4-(3,4-dihydroxyphenyl)-8-methyl-1,2,3,4-tetrahydroisoquinoline hydrobromide.

Elemental analysis (as $C_{16}H_{18}NO_3Br$)

|  | C(%) | H(%) | N(%) | Br(%) |
|---|---|---|---|---|
| Calcd. | 54.56 | 5.15 | 3.98 | 22.69 |
| Found | 54.34 | 5.10 | 3.95 | 22.58 |

Melting point: 250° C.
Mass spectrum (FAB) 272 (M+ +1)
NMR spectrum (d$_6$-DMSO, internal standard TMS)
δ(ppm): 2.05 (1H, s), 3.35 (total 3H), 6.46 (total 3H), 2.72 (total 3H, dx2)

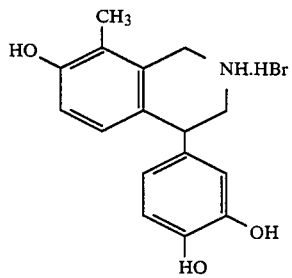

EXAMPLE 8

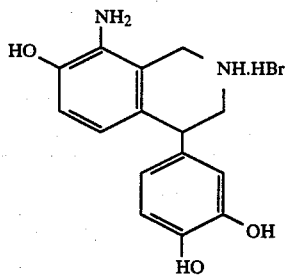

700 mg of 2-benzyl-4-(3,4-dihydroxyphenyl)-7-hydroxy-8-nitro-1,2,3,4-tetrahydroisoquinoline hydrobromide was dissolved in 14 ml of ethanol, and by adding thereto 0.07 g of 10% paradium-carbon, hydrogenation reaction was performed at 40° C. The reaction was over, the reaction mixture was filtered, and concentrated. The residue obtained was changed to precipitates by treatment with chloroform, the precipitates were collected by filtration, and dried, affording 590 mg of 8-amino-4-(3,4-dihydroxyphenyl)-7-hydroxy-1,2,3,4-tetrahydroisoquinoline hydrobromide.

Elemental analysis (as $C_{15}H_{17}N_2O_3Br$)

|  | C(%) | H(%) | N(%) | Br(%) |
|---|---|---|---|---|
| Calcd. | 51.01 | 4.85 | 7.93 | 22.62 |
| Found | 50.72 | 4.53 | 7.91 | 22.43 |

Mass spectrum (FAB) 273 ($M^+ + 1$)

NMR spectrum ($d_6$-DMSO, internal standard TMS)
δ(ppm): 5.96 (1H, d), 6.46 (1H, dd), 6.53 (1H, s), 6.60 (1H, d), 6.76 (1H, d)

EXAMPLE 9

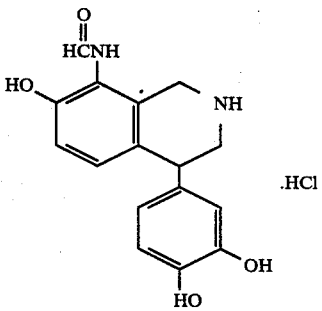

(1) 1.03 g of 2-benzyl-4-(3,4-dihydroxyphenyl)-7-hydroxy-8-nitro-1,2,3,4-tetrahydroisoquinoline hydrobromide was suspended in 20 ml of ethanol, and after adding thereto 1 ml of Raney nickel, hydrogenation reaction was performed at 40° C. The hydrogenation reaction was over, the reaction mixture was filtered, and concentrated, affording 0.88 g of 8-amino-2-benzyl-4-(3,4-dihydroxyphenyl)-7-hydroxy-1,2,3,4-tetrahydroisoquinoline hydrobromide. (2) To a solution of 0.25 ml of formic acid in 10 ml of chloroform, was added under ice cooling 0.88 g of 1-ethyl-3-(3-dimethylaminopropyl)carbodiimide, and then after 15 minutes, was added dropwise 5 ml of a solution of 8-amino-2-benzyl-4-(3,4-dihydroxyphenyl)-7-hydroxy-1,2,3,4-tetrahydroisoquinoline hydrobromide (0.88 g) in dimethylformamide. The temperature of the reaction mixture was reverted to room temperature, and the reaction was performed for further 30 minutes. The reaction mixture was concentrated, and the residue obtained was changed to precipitates by addition of standard buffer solution (x5). The precipitates were collected by filtration, and washed perfectly with water, affording 450 mg of 2-benzyl-4-(3,4-dihydroxyphenyl)-8-formylamido-7-hydroxy-1,2,3,4-tetrahydroisoquinoline.

(3) 450 mg of 2-benzyl-4-(3,4-dihydroxyphenyl)-8-formamido-7-hydroxy-1,2,3,4-tetrahydroisoquinoline was dissolved in 9 ml of ethanol, and after adding thereto 0.86 ml of 2N hydrochloric acid 0.05 g of 10% paradium-carbon, hydrogenation reaction was performed at room temperature. The hydrogenation reaction was over, the reaction mixture was filtered, and concentrated. The residue was changed to precipitates with treatment of isopropyl alcohol and acetonitrile, and the precipitates was collected by filtration, affording 320 mg of 4-(3,4-dihydroxyphenyl)-8-formamido-7-hydroxy-1,2,3,4-tetrahydroisoquinoline hydrochloride.

Elemental analysis (as $C_{16}H_{17}N_2O_4Cl$)

|  | C(%) | H(%) | N(%) | Cl(%) |
|---|---|---|---|---|
| Calcd. | 57.06 | 5.09 | 8.32 | 10.53 |
| Found | 56.78 | 4.82 | 8.20 | 10.72 |

Mass spectrum (FAB) 301 ($M^+ + 1$)

NMR spectrum ($d_6$-DMSO, internal standard TMS)
δ(ppm): 6.56 (1H, s), 6.66 (1H, d), 6.80 (1H, d), 6.90 (1H, d), 8,28 (1H, d)

EXAMPLE 10

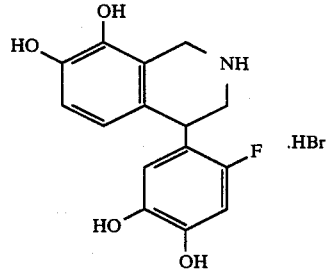

(1) α-[[(2,3-dimethoxybenzyl)amino]methyl]-6-fluoro-3,4-dimethoxybenzyl alcohol (1.0 g) was dissolved in 7 ml of trifluoroacetic acid, and after adding thereto under ice cooling, conc. sulfuric acid (0.25 ml), the mixture was stirred for 40 minutes. 0.72 g of sodium acetate was added to the reaction mixture, and the mixture was concentrated. To the residue was added chloroform and water, and the mixture was basified by addition of conc. aqueous ammonia under ice cooling. After separating procedure, the chloroform layter was collected, washed with saturated aqueous NaCl solution, and drioed over anhydrous sodium sulfate. The solvent was distilled off, 0.94 g of 4-(6-fluoro-3,4-dimethoxyphenyl)-7,8-dimethoxy-1,2,3,4-tetrahydroisoquinoline was obtained as a syrupy matter. (2) 0.90 g of 4-(6-fluoro-3,4-dimethoxyphenyl)-7,8-dimethoxy-1,2,3,4-tetrahydroisoquinoline was dissolved in 25ml of dichloromethane; and to the mixture was added dropwise 1M boron tribomide-dichloromethane solution (27 ml) under an argon gas stream, at internal temperature of −30° to −60° C. under cooling while stirring, The mixture was stirred for 3 hours at room temperature, and 7.0 ml of methanol was added to the mixture under cooling with dry ice-methanol bath, dropwise. The mixture was stirred for 30 minutes at room temperature, the crystals which separated out was collected, giving 0.75 g of 4-(6-fluoro-3,4-dihydroxyphenyl)-7,8-dihydroxy-1,2,3,4-tetrahydroisoquinoline hydrobromide.

Elemental analysis (as $C_{15}H_{15}NO_4FBr$)

|  | C(%) | H(%) | N(%) | F(%) | Br(%) |
|---|---|---|---|---|---|
| Calcd. | 48.41 | 4.06 | 3.76 | 5.10 | 21.47 |
| Found | 48.14 | 4.12 | 3.66 | 4.82 | 21.30 |

Melting point: above 238° C. (decomposition)
Mass spectrum (FAB) 292 (M$^+$+1)
NMR spectrum (d$_6$-DMSO, internal standard TMS)
δ(ppm): 5.44 (1H, m), 7.12 (1H, d), 7.43 (1H, d), 7.62 (1H, d), 7.72 (1H, d)

EXAMPLE 11

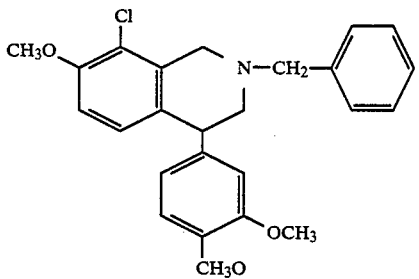
(1)

2.02 g of 8-amino-2-benzyl-7-methoxy-4-(3,4-dimethoxyphenyl)-1,2,3,4-tetrahydroisoquinoline was dissolved in 20% hydrochloric acid; and to the solution was added dropwise a solution of 0.38 g of sodium nitrite in 1.9 ml of water, under cooling. To the mixture was added dropwise a solution of 0.55 g of cuprous chloride in 11 ml of 20% hydrochloric acid. After the reaction was over, 4.84 g of sodium hydroxide was added to the mixture, and the mixture was extracted with chloroform 2 times. The chloroform layer was collected, washed with water, and dried over anhydrous magnesium sulfate. the solvent was distilled off, and the residue was recrystalllized from ethanol, giving 1.23 g of 2-benzyl-8-chloro-7-methoxy-4-(3,4-dimethoxyphenyl)-1,2,3,4-tetrahydroisoquinoline, m.p. 88°-91° C.

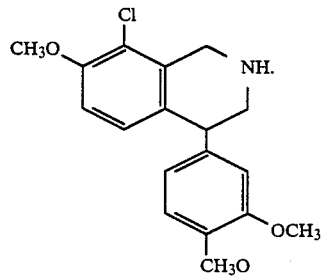
(2)

1.13 g of 2-benzyl-8-chloro-7-methoxy-4-(3,4-dimethoxyphenyl)-1,2,3,4-tetrahydroisoquinoline was dissolved in 28 ml of ethanol, and after adding thereto 0.22 ml of 12N hydrochloric acid, hydrogenation reaction was performed by addition of 0.1 g of 10%-paradium-carbon. After the hydrogenation reaction was over, the reaction solution was filtered, and concentrated. The residue was dissolved in chloroform, washed with saturated aqueous sodium hydrogen carbonate solution and water, and dried over anhydrous magnesium sulfate. The solvent was distilled off, and the residue was recrystallized from ethyl acetate-n-hexane, giving 580 mg of 8-chloro-7-methoxy-4-(3,4,-dimethoxyphenyl)-1,2,3,4-tetrahydroisoquinoline, m.p. 130°-132° C.

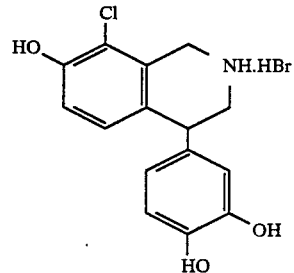
(3)

To 540 mg of 8-chloro-7-methoxy-4-(3,4-dimethoxyphenyl)-1,2,3,4-tetrahydroisoquinoline, was added 11 ml of 48% hydrobromic acid, and the mixture was heated under reflux for 3 hours under an argon gas stream. After cooling, the crystals which separated out were collected by filtration, and 520 mg of 8-chloro-7-hydroxy-4-(3,4-dihydroxyphenyl)-1,2,3,4-tetrahydroisoquinoline hydrobromide was obtained.

Elemental analysis (as $C_{15}H_{15}ClNO_3Br$)

|  | C(%) | H(%) | N(%) |
|---|---|---|---|
| Calcd. | 48.35 | 4.06 | 3.76 |
| Found | 48.32 | 4.05 | 3.75 |

Melting point: above 260° C. (decomposition)
Mass spectrum: (FAB) 292 (M$^+$+1)
NMR spectrum (d$_6$-DMSO, internal standard TMS)
δppm: 4.22 (1H, d), 6.48 (1H, dd), 6.56 (1H, s), 6.62 (1H, d), 6.75 (1H, d), 6.92 (1H, d)

EXAMPLE 12

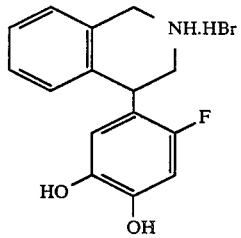

(1) α-[(benzylamino)methyl]-6-fluoro-3,4-dimethoxybenzyl alcohol (1.25 g) was dissolved in 8.75 ml of trifluoroacetic acid, and after adding thereto 0.37 ml of conc. sulfuric acid under ice-cooling, the mixture was stirred for 70 minutes. Then, 1.07 g of sodium acetate was added to the mixture, and the reaction mixture was concentrated. To the residue, was added chloroform and water, and the mixture was basified by addition of conc. aqueous ammonia under ice-cooling. By a separating procedure, the chloroform layer was collected, washed with saturated aquous NaCl solution, and dried over anhydrous sodium sulfate. The solvent was removed by distillation, giving 1.18 g of 4-(6-fluoro-3,4- dimethoxyphenyl)-1,2,3,4-tetrahydroisoquinoline as a syrupy matter.

(2) 1.15 g of 4-(6-fluoro-3,4-dimethoxyphenyl)-1,2,3,4-tetrahydroisoquinoline was dissolved in 30 ml of dichloromethane, 26.4 ml of 1M boron tribromidedichloromethane solution was added to the solution under an argon gas stream under stirring under cooling at the internal temperature of −20° to −30° C. The mixture was stirred for 3 hours at room temperature, and then, 7.0 ml of methanol was added dropwise under cooling in dry ice - methanol bath. The mixture was stirred for 30 minutes at room temperature, the crystals which separated out were collected by filtration, affording 1.0 g of 4-(6-fluoro-3,4-dihydroxyphenyl)-1,2,3,4-tetrahydroisoquinoline hydrobromide.

Elemental analysis (as $C_{15}H_{15}NO_2FBr$)

|  | C(%) | H(%) | N(%) | F(%) | Br(%) |
|---|---|---|---|---|---|
| Calcd. | 52.96 | 4.44 | 4.12 | 5.58 | 23.49 |
| Found | 52.98 | 4.50 | 4.14 | 5.62 | 23.49 |

Melting point: above 237° C. (decomposition)
Mass spectrum (FAB) 260 (M+ +1)
NMR spectrum (d6-DMSO, internal standard TMS)
δ(ppm): 3.12–3.80 (2H, m), 4.43 (2H, br-s), 4.58 (1H, dd), 6.49 (1H, d), 6.66 (1H, d), 6.84 (1H, m), 7.12–7.36 (3H, m)

EXAMPLE 13

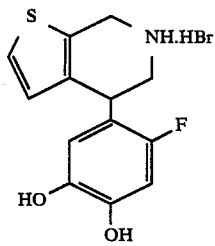

(1)

A mixture of 0.66 g of α-[[(2-thenyl)amino]methyl]-6-fluoro-3,4-dimethoxybenzyl alcohol and 10 ml of polyphosphoric acid was stirred for 3.5 hours at 60° C. The reaction solution was poured into ice water, and the mixture was basified by addition of 25 ml of conc. aqueous ammonia. The mixture was extracted with chloroform, and the chloroform layer was washed with water, and dried over anhydrous magnesium sulfate. The solvent was distilled off, and 0.66 g of 4-(6-fluoro-3,4-dimethoxyphenyl)-4,5,6,7-tetrahydrothieno[2,3-c]pyridine was obtained as a syrupy matter. (2) 0.65 g of 4-(6-fluoro-3,4-dimethoxyphenyl)-4,5,6,7-tetrahydrothieno[2,3-c]pyridine was dissolved in 14 ml of dichloromethane; and to the mixture was added 1M boron tribomide-dichloromethane solution (12 ml) dropwise under an argon gas stream, while cooling at −30°—−60° C. (internal temperature) while stirring. The mixture was stirred for 2 hours at room temperature, and 20 ml of methanol was added dropwise thereto under ice cooling. The solvent was distilled off, and the residue obtained was crystallized by using a mixture of methanol and chloroform (1:8). The crystals were collected by filtration, and recystallized from ethanol, giving 0.29 g 0f 4-(6-fluoro-3,4-dihydroxyphenyl)-4,5,6,7-tetrahydrothieno[2,3-c]pyridine hydrobromide.

Element analysis (as $C_{13}H_{13}NO_2BrFS$)

|  | C(%) | H(%) | N(%) | Br(%) | F(%) | S(%) |
|---|---|---|---|---|---|---|
| Calcd. | 45.10 | 3.78 | 4.05 | 23.08 | 5.49 | 9.26 |
| Found | 44.95 | 3.82 | 3.99 | 23.04 | 5.58 | 9.29 |

Melting point: above 237° C. (decomposition)
Mass spectrum (FAB) 266 (M+ +1)
NMR spectrum (D6-DMSO, internal standard TMS)
δ(ppm): 3.0–3.9 (2H), 4.2–4.8 (3H), 6.42 (1H, d), 6.55 (1H, d), 6.62 (1H, d), 7.47 (1H, d), 8.85 (1H, S), 9.0–10.0 (3H)

EXAMPLE 14

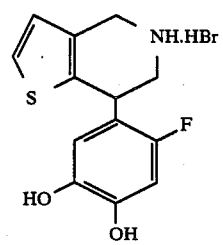

(1)

(1) 1.16 g of α-[[(-3-thenyl)amino]methyl]-6-fluoro-3,4-dimethoxybenzyl alcohol was dissolved in 11 ml of trifluoroacetic acid, and after adding thereto 0.31 ml of conc. sulfuric acid under ice cooling, the mixture was stirred for 4 hours. The reaction solution was concentrated, and chloroform and water were added to the residue. The mixture was basified by addition of 10 ml of conc. aqueous ammonia under ice cooling. The chloroform layer was collected after a separating procedure, washed with water, and dried over anhydrous magnesium sulfate. The solvent was distilled off, and the residue was recrystallized form ethanol, affording 0.76 g of 7-(6-fluoro-3,4-dimethoxyphenyl)-4,5,6,7-tetrahydrothieno[3,2-c]pyridine, m.p. 108°–111° C. (2) 0.62 g of 7-(6-fluoro-3,4-dimethoxyphenyl)-4,5,6,7-tetrahydrothieno[3,2-c]pyridine (obtained above) was dissolved in 13 ml of dichloromethane; and to the mixture was added dropwise 12 ml of 1M borontribromide-dichloromethane solution under an argon gas stream at −30°—−60° C. (internal temperature) under cooling while stirring. The mixture was stirred for 2 hours at room temperature, and to the mixture was added dropwise 20 ml of methanol under ice cooling. The solment was distilled off, and the residue was recrystallized from ethanol, affording 0.30 g of 7-(6-fluoro-3,4-hydroxyphenyl)-4,5,6,7-tetrahydrothieno[3,2-c]pyridine hydrobromide.

Elemental analysis (as $C_{13}H_{13}NO_2BrFS$)

|  | C(%) | H(%) | N(%) | Br(%) | F(%) | S(%) |
|---|---|---|---|---|---|---|
| Calcd. | 45.10 | 3.78 | 4.05 | 23.08 | 5.49 | 9.26 |
| Found | 44.97 | 3.78 | 4.01 | 23.21 | 5.46 | 9,34 |

Melting point: above 266° C. (decomposition)
Mass spectrum (FAB) 266 (M+ +1)
NMR spectrum (d6-DMSO, internal standard TMS)
δ(ppm): 3.0–3.9 (2H), 4.31 (2H, s), 4.4–4.9 (1H), 6.58 (1H, d), 6.62 (1H, d), 6.98 (1H, d), 7.49 (1H, d), 8.90 (1H, s), 9.0–10.0 (3H)

REFERENCE EXAMPLE 1'

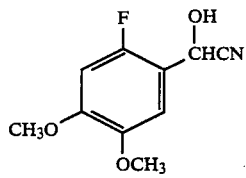

Zinc iodide (0.98 g ) was added to a solution of 6-fluoro-3,4-dimethoxybenzaldehyde (5.2 g ) in 55 ml tetrahydrofuran, trimethylsilyl-nitrile (4.92 ml ) was further added dropwise with stirring under ice cooling in an argon gas atmosphere, and stirring under ice cooling was continued for two hours. The resulting mixture was then stirred at room temperature for four hours, 4.11 ml methanol was added under ice cooling, and the solvents were distilled off. To the residue, were added 50 ml methanol and 0.65 g citric acid, and the mixture was stirred overnight at room temperature and concentrated. The residue was treated with chloroform and water, and the chloroform layer was collected and dried over anhydrous magnesium sulfate. The solvent was distilled off, and the residue was recrystallized from chloroform/n-hexane, affording 3.28 g of pure α-(cyano)-6-fluoro-3,4-dimethoxybenzyl alcohol, m.p. 112°–114° C.

REFERENCE EXAMPLE 2'

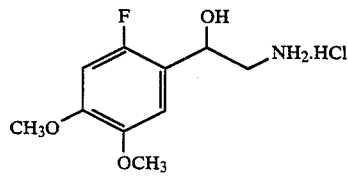

To a suspension of 3.24 g α-(cyano)-6-fluoro-3,4-dimethoxybenzyl alcohol obtained in Reference Example 1 in 20 ml tetrahydrofuran, was added dropwise 33 ml of 1M solution of borane in tetrahydrofuran with stirring in a methanol/ice bath under an argon gas atmosphere, and the resulting solution was heated under reflux for three hours. After cooling the reaction mixture in an ice bath, methanol was added until gas evolution was no longer observed, the resulting solution was stirred at room temperature for one hour, and hydrogen chloride gas was introduced until the pH fell below 1. The crystals which separated out were collected, affording 3.34 g of α-(aminomethyl)-6-fluoro-3,4-dimethoxybenyl alcohol hydrochloride, m.p. 223°–226° C.

REFERENCE EXAMPLE 3'

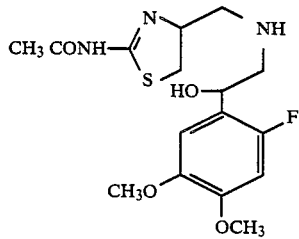

α-(Aminomethyl)-6-fluoro-3,4-dimethoxybenzyl alcohol hydrochloride (1.35 g) obtained in Reference Example 2 and 2-acetamideo-4-formyl-thiazole (1.0 g) were suspended in 6.75 ml methanol, and 0.78 ml triethylamine was added dropwise to this suspension with stirring. The resulting solution was heated under reflux for 30 minutes, and 0.30 g sodium borohydride was added in small portions with stirring under ice cooling. The crystals which separated out were collected by filtration, washed with water and methanol in that order and vaccum-dried, giving 1.22 g of α-[[[ (2-acetamido-4-thiazolyl)methyl]amino]methyl]-6-fluoro-3,4-dimethoxybenzyl alcohol, m.p. 173°–175° C.

REFERENCE EXAMPLE 4'

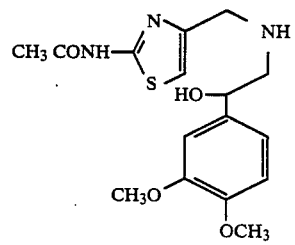

α-(Aminomethyl)-3,4-dimethoxybenzyl alcohol hydrochloride (2.88 g) and 2-acetamido-4-formyl-thiazole (2.1 g) were suspended in 14 ml methanol, and 1.8 ml triethylamine was added dropwise to this suspension with stirring. The resulting solution was heated under reflux for 30 minutes, and 0.70 g sodium borohydride was added in small portions with stirring under ice cooling. The crystals which separated out were collected by filtration, washed with water and methanol in that order and vaccum-dried, giving 3.55 g of α-[[[(2-acetamido-4-thiazolyl)methyl]amino]methyl]-3,4-dimethoxybenzyl alcohol, m.p. 204°–206° C.

EXAMPLE 15

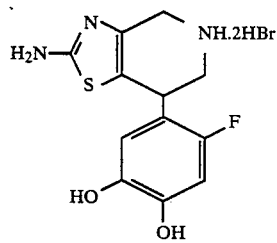

(1) A solution of 1.50 g α-[[[(2-acetamido-4-thiazolyl)methyl]amino]methyl]-6-fluoro-3,4-dimethoxybenzyl alcohol obtained in Reference Example 3 in 30 ml 6N-HCl was held at 60° C. overnight, the reaction mixture was cooled, and the crystals which separated out were collected by filtration, dissolved in 7.5 ml water and basified by addition of saturated solution of sodium bicarbonate. The crystals which separated out were collected by filtration, washed with a small amount of acetonitrile and vacuum-dried, affording 590 mg of 2-amino-7-(6-fluoro-3,4-dimethoxyphenyl)-4,5,6,7-tetrahydrothiazolo[4,5-c]pyridine, m.p. >240° C. (dec.).

(2) 2-Amino-7-(6-fluoro-3,4-dimethoxyphenyl)-4,5,6,7-tetrahydrothiazolo[4,5-c]pyridine (590 mg) obtained above was dissolved in 12 ml of 48% hydrobromic acid, and the solution was heated under reflux for three hours. The crystals which separated out were collected by filtration, affording 750 mg of 2-amino-7-(6-fluoro-3,4-dimethoxyphenyl)-4,5,6,7-tetrahydrothiazolo[4,5-c]pyridine dihydrobromide.

(i) Elemental analysis (as $C_{12}H_{14}N_3O_2SBr_2F$):

|  | C(%) | H(%) | N(%) | S(%) | Br(%) | F(%) |
|---|---|---|---|---|---|---|
| Calcd. | 32.53 | 3.18 | 9.48 | 7.24 | 36.06 | 4.29 |
| Found | 32.26 | 3.23 | 9.39 | 7.37 | 35.90 | 4.13 |

(ii) Melting point: >240° C. (dec.)
(iii) Mass spectrometry (FAB): 282 (M++1)
(iv) NMR spectrum (d$_6$-DMSO; internal standard: TMS):

(ppm) 4.25 (br-s, 2H), 4.56 (m, 1H) 6.63 (d, 1H), 6.65 (d, 1H)

EXAMPLE 16

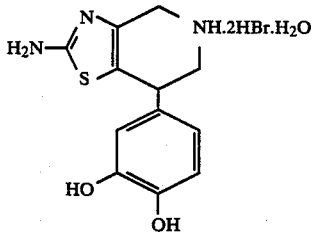

(1) A solution of 1.72 g α-[[[(2-acetamido-4-thiazolyl)methyl]amino]methyl]-3,4-dimethoxybenzyl alcohol obtained in Reference Example 4 in 34 ml 6N-HCl was held at 60° C. overnight, the reaction mixture was cooled, and the crystals which separated out were collected by filtration, dissolved in 8.5 ml water and basified by addition of saturated solution of sodium bicarbonate. The crystals which separated out were collected by filtration, washed with a small amount of acetonitrile and vacuum-dried, affording 510 mg of 2-amino-7-(3,4-dimethoxyphenyl)-4,5,6,7-tetrahydrothiazolo[4,5-c]pyridine, m.p. >240° C. (dec.).

(2) 2-Amino-4-(3,4-dimethoxyphenyl)-4,5,6,7-tetrahydrothiazolo[4,5-c]pyridine (480 mg) obtained above was dissolved in 9.6 ml of 48% hydrobromic acid, and the solution was heated under reflux for three hours. The reaction mixture was cooled, the crystals which separated out were collected by filtration, affording 620 mg of 2-amino-7-(3,4-dihydroxyphenyl)-4,5,6,7-tetrahydrothiazolo[4,5-c]pyridine dihydrobromide monohydrate.

(i) Elemental analysis (as $C_{12}H_{15}N_3O_2SBr$):

|  | C(%) | H(%) | N(%) | S(%) | Br(%) |
|---|---|---|---|---|---|
| Calcd. | 32.52 | 3.87 | 9.48 | 7.24 | 36.06 |
| Found | 32.27 | 3.71 | 9.43 | 7.25 | 36.34 |

(ii) Melting point: >250° C. (dec.)
(iii) Mass spectrometry (FAB): 264 (M++1)
(iv) NMR spectrum (D$_6$-DMSO, internal standard: TMS):

(ppm) 6.56 (dd, 1H), 6.68 (d, 1H) 6.76 (d, 1H)

PRESCRIPTION

A mixture of 100 mg of the compound obtained in Example 6 or 7 (free base), 200 mg of crystalline lactose and 2 mg of magnesium stearate is filled in a capsule by the usual method, and is orally administered four times a day to a patient requiring dilation of renal vascular tracts.

EXAMPLE 17

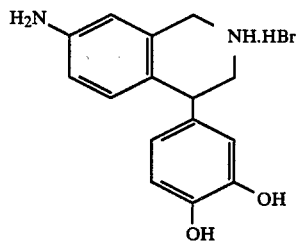

(1) A solution of 2.8 g α-[(3-aminobenzylamino)methyl]-3,4-dimethoxybenzyl alcohol obtained in Reference Example 2 in 15 ml 6N-HCl was held at 60° C. overnight with stirring, and the reaction mixture was stirred under ice cooling for one hour. The crystals which separated out were collected by filtration, chloroform and water were added, and 10% aqueous solution of caustic soda was further added under ice cooling until the aqueous layer became alkaline. The mixture was stirred well, and the chlorofrm layer was collected, washed with saturated aqueous solution of sodium chloride and dried over anhydrous sodium sulfate. The solvent was distilled off, and the residue was recrystallized from ethyl acetate/n-hexane, affording 1.5 g of pure 7-amino-4-(3,4-dimethoxyphenyl)-1,2,3,4-tetrahydroisoquinoline, m.p. 157°-159° C.

(2) To a solution of 1.5 g 7-amino-4-(3,4-dimethoxyphenyl)-1,2,3,4-tetrahydroisoquinoline obtained above in 50 ml dichloromethane, was added dropwise 1M solution of boron tribromide in dichloromethane (25 ml) under an argon gas stream while maintaining the internal temperature at −20° C. The reaction mixture was stirred at room temperature for three hours and then cooled to −20° C. once again, and 7 ml methanol was added dropwise at that temperature. The crystals which separated out were collected by filtration and recrystallized from ethanol, giving 1 g of pure 7-amino-4-(3,4-dimethoxyphenyl)-1,2,3,4-tetrahydroisoquinoline dihydrobromide.

(i) Elemental analysis (as $C_{15}H_{18}Br_2N_2O_2$):

|  | C(%) | H(%) | N(%) | Br(%) |
|---|---|---|---|---|
| Calcd. | 43.09 | 4.34 | 6.70 | 38.22 |
| Found | 43.36 | 4.59 | 6.50 | 37.89 |

(ii) Melting point: 194°-196° C. (dec.)
(iii) Mass spectrometry (FAB): 257 (M++1)
(iv) NMR spectrum (D$_6$-DMSO; internal standard: TMS):

δ(ppm) 6.56 (s, 2H), 6.72 (d, 1H) 6.92 (d, 1H), 7.12 (s, 2H)

PRESCRIPTION

A mixture of 100 mg of the compound obtained in Example 18 (free base), 200 mg of crystalline lactose and 2 mg of magnesium stearate is filled in a capsule by the usual method, and is orally administered four time a day to a patient requiring dilation of renal vascular tracts.

REFERENCE EXAMPLE

To a suspension of 22.5 g of methanesulfonylamidobenzoic acid in 648 ml of dichloromethane, was added 24,37 g of 1-ethyl-3-(3-dimethylaminopropyl)carbodiimide hydrochloride with stirring under ice-cooling, and stirring under ice-cooling was continued for 50 minutes. To the resulting mixture was added a suspension of 24.37 g of α-(aminomethyl)-3,4-dimethoxybenzyl alcohol hydrochloride and 15.14 ml of N-methylmorpholine in 100 ml of dichloromethane in small portions, and stirring under ice-cooling was continued for 5 hours. To the resulting mixture was added 1 N HCl (300 ml), and the dichloromethane layer was separated. The separated solution was washed once with each of 1N HCl and saturated aqueous NaCl solution, and dried over anhydrous magnesium sulfate. The solvent was distilled off, and 32.71 g of α-(N-(3-methanesulfonylamidobenzolyl)amidomethyl]-3,4-dimethoxybenzyl alcohol was obtained as foamy matter.

REFERENCE EXAMPLE 32.7 g of α-[N-(3-methanesulfonylamidobenzolyl)amidomethyl]-3,4-dimethoxybenzyl alcohol was dissolved in 250 ml of tetrahydrofurane. To the resulting solution was added 298 ml of 1M borane-tetrahydrofurane dropwise below −30° C. The temperature of the resulting solution was raised to room temperature, and the solution was heated under reflux for 2.5 hours. To the resulting solution was added 24.9 ml of conc. hydrochloric acid dropwise, and the solution was stirred for 30 minutes at room temperature. The solvent was distilled off; and to the residue obtained were added water and chloroform. The resulting mixture was basified with conc. aqueous ammonia, and extracted thrice with chloroform. The chloroform layers were combined, washed with saturated aqueous NaCl solution, and dried over anhydrous magnesium sulfate. The solvent was distilled off, and the residue thus obtained was subjected to silica gel column chromatography (chloroform-methanol-28% aqueous ammonia=20:1:0.1∼10:1:0.1), and a material of Rf being 0.12 [Kiesel gel 60F$_{254}$ plate; chloroform-methanol-28% aqueous ammonia (20:1:0.1)] was collected, and crystallized from chloroformn-hexane, affording 12.73 g of α-[[(3-methanesulfonylamidobenzyl)amino]methyl]-3,4-dimethoxybenzyl alcohol, m.p. 98°-100° C.

EXAMPLE 18

(1) 12.7 g of α-[[(3-methanesulfonylamidobenzyl)amino]methyl]-3,4-dimethoxybenzyl alcohol was dissolved in 250 ml of 6N hydrochloric acid, the mixture was allowed to react under an argon gas stream at 60°-65° C. for 3 hours. To the cooled reaction mixture was added chloroform, ice and conc. aqueous ammonia; and the mixture was extracted with 5% methanol-chloroform under basic condition. The organic layer was washed with saturated aqueous NaCl solution, and dried over anhydrous magnesium sulfate. The solvent was distilled off, and the residue thus obtained was subjected to silica gel column chromatography (chlroform-methanol-28% aqueous ammonia=20:1:0.1∼10:1:0.1), and a material of Rf being 0.14 [Kiesel gel 60F$_{254}$ plate; chloroform-methanol-28% aqueous ammonia=20:1:0.1) was collected, and crystallized from chloroform-ether, affording 5.94 g of 4-(3,4-dimethoxyphenyl)-7-methanesulfonylamido-1,2,3,4-tetrahydroisoquinoline, m.p. 220°-222° C. (2)

4.0 g of 4-(3,4-dimethoxyphenyl)-7-methanesulfonylamido-1,2,3,4-tetrahydroisoquinoline was suspended in 40 ml of dichloromethane, and after adding thereto 20.8 ml of acetic anhydride under an argon gas stream at room temperature, the mixture was allowed to react for 1 hour. To the reaction solution were added water, ice and conc. aqueous ammonia, the mixture was extracted with dichloromethane under basic condition; and the extract was washed with 1N hydrochloric acid and water, each once, and dried over anhydrous magnesium sulfate. The solvent was distilled off, and 4.46 g of 2-acetyl-4-(3,4-dimethoxyphenyl)-7-methanesulfonylamido-1,2,3,4-tetrahydroisoquinoline was obtained a a syrupy matter. (3)

4,46 g of 2-acetyl-4-(3,4-dimethoxyphenyl)-7-methanesulfonylamido-1,2,3,4-tetrahydroisoquinoline (obtained at (2) above) was dissolved in 50 ml of dichloromethane; and to the solution was added 66.2 ml of 1M-borane-3Br dichloromethane solution dropwise under cooling below −28° C. under an argon gas stream. The mixture was allowed to react for 2.5 hours, and after adding dropwise 13.96 ml of methanol below −40° C., the temperature of the reaction solution was raised upto room temperature. About 30 ml of methanol was added to the solution, and the solvent was distilled off. 50 ml of toluene was added to the residue obtained, and the solvent was distilled off again, and after adding to the residue water and ethyl acetate, the mixture was extracted with ethyl acetate. The extract was washed with water and saturated aqueous NaCl solution each once, and dried over anhydrous magnesium sulfate. The solvent was distilled off, and 4.13 g of 2-acetyl-4-(3,4-dihydroxyphenyl)-7-methanesulfonylamido-1,2,3,4-tetrahydroisoquinoline was obtained, m.p. 125°-127° C. (4)

1.7 g of 2-acetyl-4-(3,4-dihydroxyphenyl)-7-methanesulfonylamido-1,2,3,4-tetrahydroisoquinoline obtained at (3) above was dissolved in 17 ml of ethanol and 17 ml of 2N hydrochloric acid, and the mixture was heated under reflux under an argon gas stream for 8.5 hours. The solvent was distilled off, and after adding water and ethyl acetate, the aqueous layer was separated with a separating funnel. The aqueous layer was washed with ethyl acetate 5 times, and concentrated. To the residue was added 30 ml of ethanol, and concentrating procedures was conducted 3 times, and after drying, 1.12 g of 4-(3,4-dihydroxyphenyl)-7-methanesulfonylamido-1,2,3,4-tetrahydroisoquinoline HCl salt was obtained a foamy matter.

Elemental analysis (as $C_{16}H_{18}N_2O_4SCl.1/3H_2O$)

|  | C(%) | H(%) | N(%) | S(%) | Cl(%) |
|---|---|---|---|---|---|
| Calcd. | 50.99 | 5.26 | 7.43 | 8.50 | 9.40 |
| Found | 51.20 | 5.31 | 7.29 | 8.73 | 9.63 |

Mass spectrometry (FAB): 335 (M +1)

NMR spectrum (D$_6$-DMSO; internal standard: TMS) δ(ppm) 3.02 (3H, s), 3.1-3.7 (2H, m) 4.24 (1H, m), 3.35 (2H, br-s) 6.4-72. (6H, m)

REFERENCE EXAMPLE 32

(1) 12.0 g of 3-ethanesulfonylamidobenzoic acid was suspended in 360 ml of dichloromethane, and after adding thereto under ice cooling while stirring 12.04 g of 1-ethyl-3-(3-dimethylaminopropyl)carbodiimide hydrochloride, the mixture was stirred for 30 minutes. To the mixture was added a suspension of 12.23 g of α-(aminomethyl)-3,4-dimethoxybenzyl alcohol hydrochloride and 7.48 ml of N-methylmorpholine in 60 ml of dichloromethane, slowly. The mixture was stirred overnight under ice cooling. After adding 1N hydrochloric acid (200 ml), the dichloromethane layer was collected, washed with 1N hydrochloric acid and saturated aqueous NaCl solution each once, and dried over anhdyrous magnesium sulfate. The solvent was distilled off, giving 20.35 g of α-[N-(3-ethanesulfonylamidobenzoyl)amidomethyl]-3,4-dimethoxybenzyl alcohol as a foamy matter.

(2) 20.0 g of α-[N-(3-ethanesulfonylamidobenzoyl)amidomethyl]-3,4-dimethoxybenzyl alcohol was dissolved in 150 ml of tetrahydrofuran; and to the mixture was added dropwise 1M borane-tetrahydrofuran solution (176 ml) below −20° C. The temperature of the solution was raised gradually to room temperature, and the mixture was heated under reflux for 2.5 hours. To the mixture was added 7.13 ml of methanol under cooling with methanol-ice bath, and the mxiture was heated under reflux for 30 minutes. To the solution was added 14.7 ml of conc-hydrochloric acid under cooling with methanol-ice bath, dropwise, and the mixture was stirred at room temperature for 30 minutes, and the solvent was distilled off. To the residue was added water and chloroform, and the mixture was basified with conc. aqueous ammonia, and extracted with choroform 3 times. The chloroform layer was collected, washed with saturated aqueous NaCl solution, and dried over anhdyrous magnesium sulfate. The solvent was distilled off, and the residue was subjected to column chromatography (chloroform-methanol-28% aqueous ammonia=20:1:0.1–10:1:0.1), and a materia of Rf being 0.13 [Kiesel gel 60F$_{254}$ plate, chloroform-methanol-28% aqueous ammonia=20:1:0.1) was collected, giving 13.81 g of alpha-[[(3-ethanesulfonylamidobenzyl)amino]methyl]-,4-dimethoxybenzyl-alcohol.

EXAMPLE 19

1.0 g of 2-acetyl-4-(3,4-dihydroxyphenyl)-7-ethanesulfonylamido-1,2,3,4-tetrahydroisoquinoline was dissolved in 10 ml of ethanol and 10 ml of 2N hydrochloric acid, and the mixture was heated under reflux overnight. The solvent was distilled off, and after adding water and ethyl acetate, the aqueous layer was collected, washed with ethyl acetate twice, and concentrated. To the residue was added 30 ml of ethanol, and the concentration procedures were repeated 3 times. The residue was crystallized from isopropanol, giving 0.90 g of 4-(3,4-dihydroxyphenyl)-7-ethanesulfonylamido-1,2,3,4-tetrahydroisoquinoline.1-isopropanol.1-HCl salt.

Melting point: 161°–162° C.

Elemental analysis (as $C_{17}H_{21}N_2O_4xSCl.C_3H_7OH$)

|  | C(%) | H(%) | N(%) | S(%) | Cl(%) |
|---|---|---|---|---|---|
| Calcd. | 53.98 | 6.57 | 6.30 | 7.21 | 7.97 |
| Found | 53.74 | 6.50 | 6.25 | 7.29 | 8.17 |

Mass spectrum (FAB) 349 (M +1)

NMR spectrum (d$_6$-DMSO, internal standard TMS) (ppm): 1.21 (3H, t), 3.10(2H, t), 3.2–3.9(2H, m), 4.20(1H, m), 4.34(2H, br-s), 6.4–7.2(6H, m)

The starting material of the above compound has melting point of 117°–119° C., and was prepared by a conventional manner.

The the following copounds were also prepared.
4-(3,4-dimethoxyphenyl)-7-ethanesulfonylamido-1,2,3,4-tetrahydroisoquinoline, m.p. 209°–211° C.

2-acetyl-4-(3,4-dimethoxyphenyl)-7-ethanesulfonylamido-1,2,3,4-tetrahdydroisoquinoline (a foamy matter).

We claim:

1. A compound of the Formula (I):

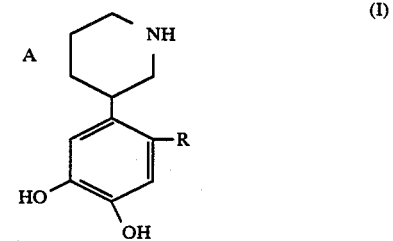

wherein

A represents the formula

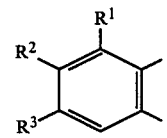

wherein $R^1$ is hydrogen, lower alkyl, hydroxyl, halogen, amino or lower acylamino;

$R^2$ is hydrogen, lower alkyl, hydroxyl, amino or lower alkylsulfonylamino;

$R^3$ is hydrogen, lower alkyl or hydroxyl;

R is hydrogen or halogen, with the proviso that when $R^1$ is other than lower alkyl, there is no case that all of $R^2$, $R^3$ and. R are hydrogens; or a salt thereof.

2. A compound according to claim 1 which is 7,8-dihydroxy-4-(3,4-dihydroxyphenyl)-1,2,3,4-tetrahydroisoquinoline or its salt.

3. A compound according to claim 1 which is 7-hydroxy-4-(3,4-dihydroxyphenyl)-8-methyl-1,2,3,4-tetrahydroisoquinoline or its salt.

4. A compound according to claim 1 which is 4-(3,4-dihydroxyphenyl)-7-methanesulfonylamido-1,2,3,4-tetrahydroisoquinoline or its salt.

5. A pharmaceutical composition useful for dilating nephrovascular tracts, said composition comprised of from about 50 to about 1,000 milligrams of the compound of claim 1 and a pharmaceutically acceptable carrier.

6. The pharmaceutical composition of claim 5, wherein said compound is 7,8-dihydroxy-4-(3,4-dihydroxyphenyl)-1,2,3,4-tetrahydroisoquinoline or its salt.

7. The pharmaceutical composition of claim 5, wherein said compound is 7-hydroxy-4-(3,4-dihydroxyphenyl)-8-methyl-1,2,3,4-tetrahydroisoquinoline or its salt.

8. The pharmaceutical composition of claim 5, wherein said compound is 4-(3,4-dihydroxyphenyl)-7-methanesulfonylamido-1,2,3,4-tetrahydroisoquinoline or its salt.

* * * * *

UNITED STATES PATENT AND TRADEMARK OFFICE
CERTIFICATE OF CORRECTION

PATENT NO. : 4,876,261

DATED : October 24, 1989

INVENTOR(S) : Akihiro Tanaka, et al

It is certified that error appears in the above-identified patent and that said Letters Patent is hereby corrected as shown below:

ON THE TITLE PAGE:

The firm of "BURGESS, RYAN AND WAYNE" should be listed as the Attorneys of Record.

IN THE ABSTRACT:

Line 7: (after the third formula) "lower, alkyl" should read --lower alkyl--.

Claim 1, Column 38, lines 10-25: the letter "A" in both occurrences should be encircled.

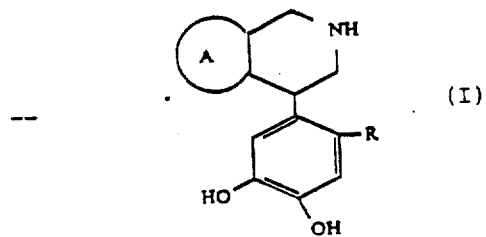

wherein

--

Signed and Sealed this

Twenty-sixth Day of May, 1992

Attest:

DOUGLAS B. COMER

*Attesting Officer*  *Acting Commissioner of Patents and Trademarks*